United States Patent
Wurzbach et al.

(10) Patent No.: US 9,482,506 B1
(45) Date of Patent: Nov. 1, 2016

(54) METHODS AND APPARATUS FOR NON-CONTACT INSPECTION OF CONTAINERS USING MULTIPLE SENSORS

(75) Inventors: James A. Wurzbach, San Diego, CA (US); Courtney Konopka, Carlsbad, CA (US); Manuel T. Silvia, Ojai, CA (US)

(73) Assignee: Raytheon Company, Waltham, MA (US)

( * ) Notice: Subject to any disclaimer, the term of this patent is extended or adjusted under 35 U.S.C. 154(b) by 411 days.

(21) Appl. No.: 13/418,814

(22) Filed: Mar. 13, 2012

Related U.S. Application Data

(63) Continuation of application No. 61/452,419, filed on Mar. 14, 2011.

(51) Int. Cl.
- *G06K 9/00* (2006.01)
- *F42D 1/05* (2006.01)
- *B60N 2/00* (2006.01)

(52) U.S. Cl.
CPC .............. *F42D 1/05* (2013.01); *G06K 9/00362* (2013.01); *B60N 2/002* (2013.01); *G06K 9/00832* (2013.01)

(58) Field of Classification Search
CPC ..................... G06K 9/00362; G06K 9/00832; B60N 2/002
USPC ......................................................... 600/508
See application file for complete search history.

(56) References Cited

U.S. PATENT DOCUMENTS

| | | |
|---|---|---|
| 4,415,979 A | 11/1983 | Hernandez |
| 4,855,911 A | 8/1989 | Lele et al. |
| 5,333,129 A | 7/1994 | Buckingham |
| 5,760,887 A | 6/1998 | Fink et al. |
| 5,790,032 A | 8/1998 | Schmidt |
| 5,821,424 A | 10/1998 | Rodriguez |
| 5,974,881 A | 11/1999 | Donskoy et al. |
| 5,979,240 A | 11/1999 | Rix et al. |
| 6,081,481 A | 6/2000 | Sabatier et al. |
| 6,370,481 B1 | 4/2002 | Gamble |
| 6,650,685 B2 | 11/2003 | Halmos et al. |
| 6,870,791 B1 | 3/2005 | Caulfield et al. |
| 6,932,769 B2 | 8/2005 | Griffin et al. |
| 6,972,846 B2 | 12/2005 | Lal et al. |
| 7,116,426 B2 | 10/2006 | Lal et al. |
| 7,468,672 B2 | 12/2008 | Harden et al. |
| 7,477,398 B2 | 1/2009 | Lal et al. |
| 7,477,758 B2 | 1/2009 | Piirainen et al. |
| 7,492,449 B2 | 2/2009 | Ume et al. |
| 7,535,355 B2 | 5/2009 | Barone |

(Continued)

OTHER PUBLICATIONS

J.M. Sabatier, H.E. Bass, and L.N. Bolen, "The Interaction of Airborne Sound With the Porous Ground: The Theoretical Formulation", J. Acoustic. Soc. Am. 79(5), pp. 1345-1352 (1986).

(Continued)

*Primary Examiner* — Joseph Dietrich
(74) *Attorney, Agent, or Firm* — Daly, Crowley, Mofford & Durkee, LLP

(57) ABSTRACT

Methods and apparatus for an acoustic source for directing acoustic energy to ensonify a container, a first sensor to detect acoustic energy from the acoustic source affected by an object in the container without contacting the container, a second sensor to confirm presence of the object, and a processing module to process the detected acoustic energy from the first and second sensors to identify the object in the container.

20 Claims, 34 Drawing Sheets

(56) References Cited

U.S. PATENT DOCUMENTS

| | | | |
|---|---|---|---|
| 7,599,253 B1 | 10/2009 | Huang | |
| 7,613,075 B2 | 11/2009 | Cray et al. | |
| 7,894,305 B2 | 2/2011 | Sabatier et al. | |
| 8,151,644 B2 | 4/2012 | Brandt et al. | |
| 8,531,915 B2 | 9/2013 | Ammar | |
| 2002/0024331 A1 | 2/2002 | Lewis et al. | |
| 2003/0204290 A1* | 10/2003 | Sadler et al. | 701/1 |
| 2005/0012935 A1* | 1/2005 | Kersey | G01B 11/161 356/519 |
| 2006/0139162 A1 | 6/2006 | Flynn | |
| 2006/0225509 A1 | 10/2006 | Haupt et al. | |
| 2006/0251293 A1* | 11/2006 | Piirainen et al. | 382/104 |
| 2007/0166049 A1 | 7/2007 | Pearson et al. | |
| 2008/0245150 A1 | 10/2008 | Katayama et al. | |
| 2008/0249722 A1 | 10/2008 | Meitzner | |
| 2009/0007670 A1 | 1/2009 | Hawwa et al. | |
| 2009/0046296 A1 | 2/2009 | Kilpatrick et al. | |
| 2010/0278008 A1* | 11/2010 | Ammar | G01S 7/521 367/7 |
| 2011/0140885 A1* | 6/2011 | Hummer et al. | 340/539.13 |
| 2011/0141283 A1 | 6/2011 | Lee et al. | |

OTHER PUBLICATIONS

J.M. Sabatier, H.E. Bass, and L.N. Bolen, and K. Attenborough, "Acoustically Induced Seismic Waves", J. Acoustic. Soc. Am. 80(2), pp. 646-649 (1986).

J.M. Sabatier, H.E. Bass, and G.R. Elliot, "On the Location of Frequencies of Maximum Acoustic-To-Seismic Coupling", J. Acoustic. Soc. Am. 80(4), pp. 1200-1202 (1986).

J.M. Sabatier and N. Xiang, "An Investigation of Acoustic-To-Seismic Coupling to Detect Buried Anti-Tank Landmines", IEEE Trans. on Geoscience and Remote Sensing, 39(6), pp. 1146-1154 (2001).

N. Xiang and J.M. Sabatier, "Bayesian Probability Analysis for Acoustic-To-Seismic Landmine Detection", J. Acoust. Soc. Am. 112(5), pp. 2390-2391 (2002).

N. Xiang and J.M. Sabatier, "An Experimental Study on Anti-Personnel Landmine Detection Using Acoustic-To-Seismic Coupling", J. Acoust. Soc. Am. 113(3), pp. 1333-1341 (2003).

D. Velea, R. Waxler, and J.M. Sabatier, "An Effective Fluid Model for Landmine Detection Using Acoustic-To-Seismic Landmine Detection", J. Acoust. Soc. Am. 115(5), pp. 1993-2002 (2004).

M.S. Korman, and J.M. Sabatier, "Nonlinear Acoustic Techniques for Landmine Detection", J. Acoust. Soc. Am. 116(6), pp. 3354-3369 (2004).

R.W. Haupt and K.D. Rolt, "Standoff Acoustic Laser Technique to Locate Buried Mines", MIT Lincoln Laboratory Journal, 15(1), pp. 3-22 (2005).

B.A. Cray, S.E. Forsyth, A.J. Hull, and L.E. Estes, "A Scanning Laser Doppler Vibrometer Acoustic Array", J. Acoust. Soc. Am. 120(1), pp. 164-170 (2006).

M.A. Biot, "Theory of Elasticity and Consolidation for a Porous Anisotropic Solid", J. Appl. Phys. 26, pp. 182-185 (1955).

J.E. Piper, K.W. Commander, E.I. Thorsos, and K.L. Williams, "Detection of Buried Targets Using Synthetic Aperture Sonar", IEEE J. of Ocean Engineering, 27(3), pp. 495-503 (2002).

D. Stemlicht and J.F. Pesaturo, "Synthetic Aperture Sonar: Frontiers in Underwater Imaging", Sea Technology, November, pp. 27-32 (2004).

M.T. Silvia and A.B. Weglein, "Method for Obtaining a Near-Field Inverse Scattering Solution to the Acoustic Wave Equation", J. Acoust. Soc. Am. 69(2), pp. 478-482 (1981).

A.B. Weglein and M.T. Silvia, "Scattering Theory Approach to the Identification of the Helmholtz equation: A Nearfield Solution", J. Acoust. Soc. Am. 69(2), pp. 483-488 (1981).

James G. Berryman and R.R. Greene, "Discrete Inverse Methods for Elastic Waves in Layered Media", Geophysics 45(2), pp. 213-233 (1980).

Response to Office Action filed May 27, 2015 for U.S. Appl. No. 13/418,807; 11 pages.

Response to Office Action filed May 15, 2015 for U.S Appl. No. 13/418,799; 16 pages.

Office Action dated Aug. 27, 2015 for U.S. Appl. No. 13/418,799; 40 pages.

Office Action dated Sep. 11, 2015 for U.S. Appl. No. 13/418,807, 19 pages.

Response to Office Action filed Sep. 26, 2014 for U.S. Appl. No. 13/418,807; 13 pages.

Office Action dated Oct. 8, 2014 for U.S. Appl. No. 13/418,807; 20 pages.

Response to Office Action filed Jan. 8, 2015 for U.S. Appl. No. 13/418,807; 6 pages.

Office Action dated Jan. 27, 2015 for U.S. Appl. No. 13/418,807; 16 pages.

Office Action dated Mar. 10, 2016 for U.S. Appl. No. 13/418,807; 18 pages.

Response to Office Action filed Sep. 15, 2014 for U.S. Appl. No. 13/418,799; 12 pages.

Office Action dated Dec. 17, 2014 for U.S. Appl. No. 13/418,799; 31 pages.

Response to Office Action filed Dec. 28, 2014 for U.S. Appl. No. 13/418,799; 20 pages.

Notice of Allowance dated Apr. 20, 2016 for U.S. Appl. No. 13/418,799; 19 pages.

U.S. Appl. No. 13/418,799, Office Action dated Mar. 13, 2014, 32 pages.

Maurer et al., "Laser Doppler Vibrometry"; 9c) 2010, Carl Hanser Verlag; Munich, Germany, 4 pages.

U.S. Appl. No. 13/418,807 Office Action dated Mar. 26, 2014, 24 pages.

GA Dept. of Transportation, "Sensing System Development for HOV/HOT (High Occupancy Vehicle) Lane Monitoring", GDOT Research Project No. RP 07-26, Feb. 2011. 101 pages.

Notice of Allowance dated Jun. 17, 2016 for U.S. Appl. No. 13/418,807, 22 pages.

* cited by examiner

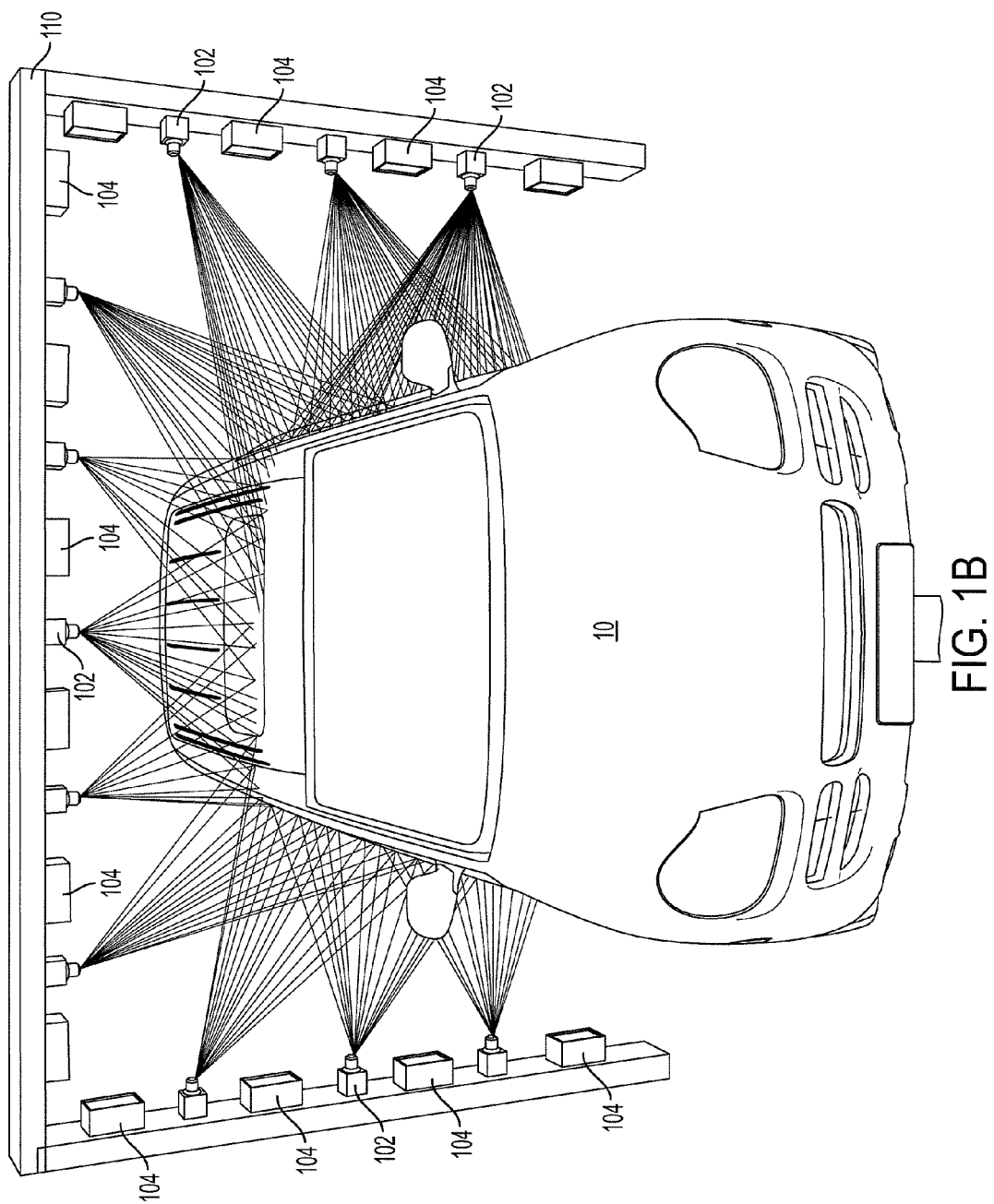

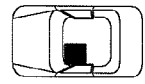
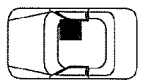
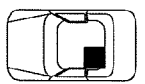
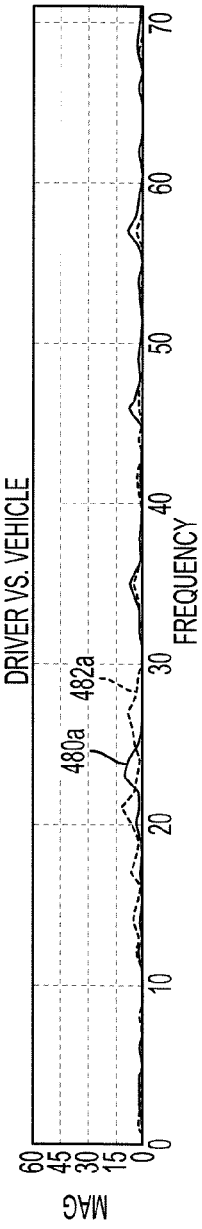
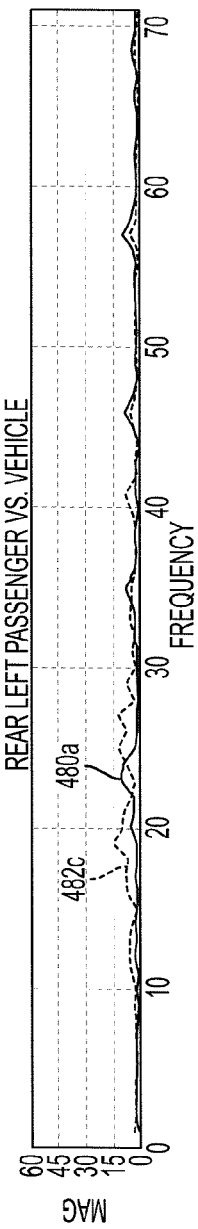
FIG. 12A
FIG. 12B
FIG. 12C

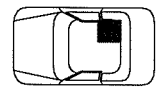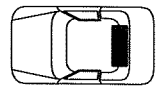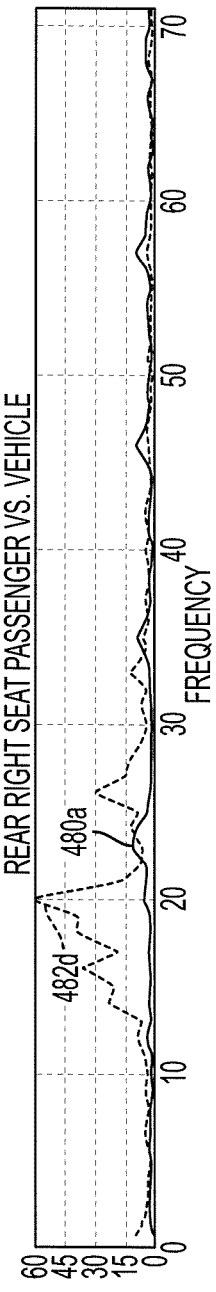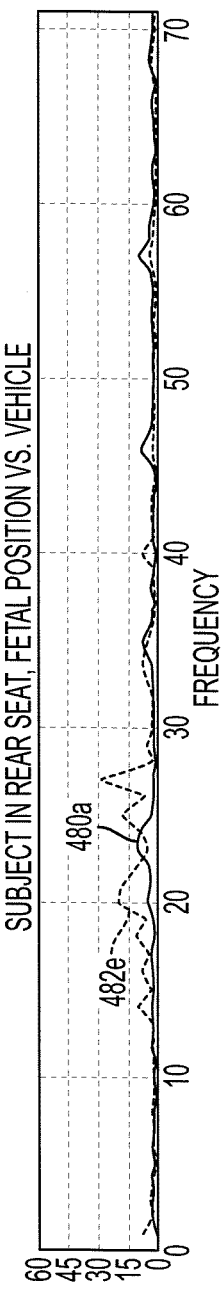
FIG. 12D
FIG. 12E

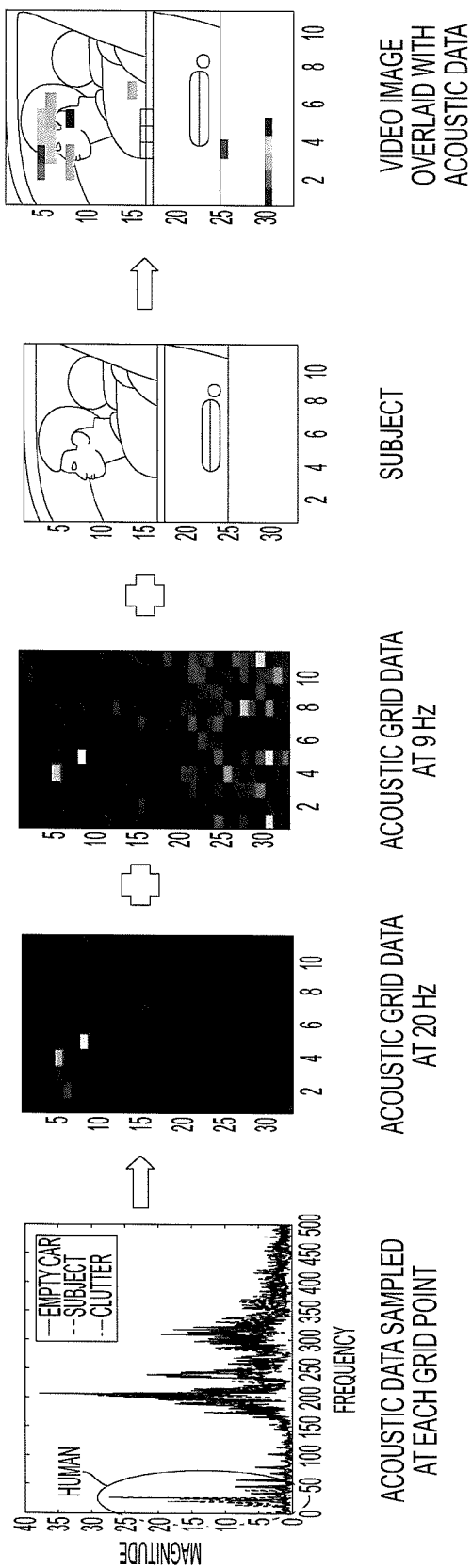

METHODS AND APPARATUS FOR NON-CONTACT INSPECTION OF CONTAINERS USING MULTIPLE SENSORS

CROSS REFERENCE TO RELATED APPLICATIONS

The present application claims the benefit of U.S. Provisional Application No. 61/452,419, filed on Mar. 14, 2011, which is incorporated herein by reference.

BACKGROUND

Vehicular checkpoints are a familiar and widely used method for securing national borders around the world. In the United States, vehicular inspections at border checkpoints are typically executed in three phases: pre-inspection, primary inspection and optional secondary inspection. In the pre-inspection phase, canine units perform a random inspection in traffic lanes on waiting vehicles to detect indications of smuggling. Other techniques, such as video surveillance and radiation monitoring, etc., may also be employed.

Suspicious vehicles are flagged for additional scrutiny during the primary inspection phase. During this phase, a vehicle driver may be briefly questioned and documentation checked. The driver may also be evaluated for indications that a secondary inspection is warranted. These interviews usually last only 10-15 seconds per vehicle, but can back traffic up for miles, causing border delays of hours.

In the optional secondary inspection phase, the driver and vehicle undergo closer scrutiny, which may take 20-30 minutes, or even longer in some cases. As inspection resources are limited, the goal of the inspection process is to maximize the productivity and safety of the secondary search phase. It will be appreciated that a low false alarm rate to trigger the secondary search phase is desirable.

A variety of well-known systems are used at checkpoints and border crossings. For example, X-ray backscatter systems can be used to inspect trucks at border crossings. However, these systems are slow, are range-limited, employ ionizing radiation, and are expensive. Further, as "backscatter" is really reflected radiation, any detected items will obscure or mask items behind them. Geophones, stethoscopes, and other hand-held detection devices are also used, but require intimate contact with the vehicle or container. As these inspection techniques are time-intensive, they are typically used on only a sampling of containers, as well as for vehicles selected for secondary inspections.

Canine inspections can be effective, but require close proximity of dogs to vehicles and may take significant time. Canines also require handlers to provide these dogs with constant care and supervision. In addition, these dogs require periodic re-certification, and they become less effective over time. Further, a canine's effective endurance can be as little as fifteen minutes in inclement weather.

SUMMARY

The present invention provides methods and apparatus for inspecting the interior of a container or passing vehicle, e.g., a passenger car, using an acoustic source of sufficiently low frequency so as to effect penetration and ensonification of the subject container or vehicle. The resultant acoustic energy is sampled at the surface of the vehicle using a detector, such as a scanning laser vibrometer, which creates a kind of dynamic virtual microphone array. The collected data is then processed to identify frequency response profiles for detecting, identifying and localizing objects of interest, e.g., human trafficking, contraband and explosive cargo.

While exemplary embodiments of the invention are shown and described in conjunction with searching vehicles at checkpoints and border crossings, it is understood that embodiments of the invention are applicable to detection systems in general, in which, it is desirable to identify objects of interest in a contained volume which can be ensonified and a surface which can be sampled using an acoustic sensor, such as a laser vibrometer.

In one aspect of the invention, a system comprises an acoustic source for directing acoustic energy to ensonify a container, a sensor to detect acoustic energy from the acoustic source affected by an object in the container without contacting the container, and a processing module to process the detected acoustic energy from the sensor to identify the object in the container.

In another aspect of the invention, a method comprises directing acoustic energy at a container to ensonify the container, detecting acoustic energy affected by an object in the container without contacting the object, and processing the detected acoustic energy from the sensor to identify the object.

In another aspect of the invention, a system comprises an acoustic source for directing acoustic energy to ensonify a container containing an object, a sensor to detect acoustic energy from the acoustic source affected by the object without contacting the container, and a processing module to process the detected acoustic energy from the sensor to generate an image of the object.

In another aspect of the invention, a method comprises directing acoustic energy to ensonify a container containing an object, detecting acoustic energy affected by the object without contacting the container, and processing the detected acoustic energy to generate an image of the object.

In another aspect of the invention, a system comprises an acoustic source for directing acoustic energy to ensonify a container, a first sensor to detect acoustic energy from the acoustic source affected by an object in the container without contacting the container, a second sensor to confirm presence of the object, and a processing module to process the detected acoustic energy from the sensor to identify the object in the container.

In another aspect of the invention, a method comprises directing acoustic energy to ensonify a container, detecting, by a first sensor, acoustic energy from the acoustic source affected by an object in the container without contacting the container, using a second sensor to detect the object in the container, and processing the detected acoustic energy and information from the first and second sensors to identify the object in the container.

BRIEF DESCRIPTION OF THE DRAWINGS

The foregoing features of this invention, as well as the invention itself, may be more fully understood from the following description of the drawings in which:

FIG. 1B is a schematic representation of an acoustic inspection system in accordance with exemplary embodiments of the invention;

FIGS. 12a-e show acoustic responses for a human at various locations in a vehicle;

FIGS. 13a-e shows acoustic images at respective frequencies and corresponding video images;

DETAILED DESCRIPTION

Figure 1:
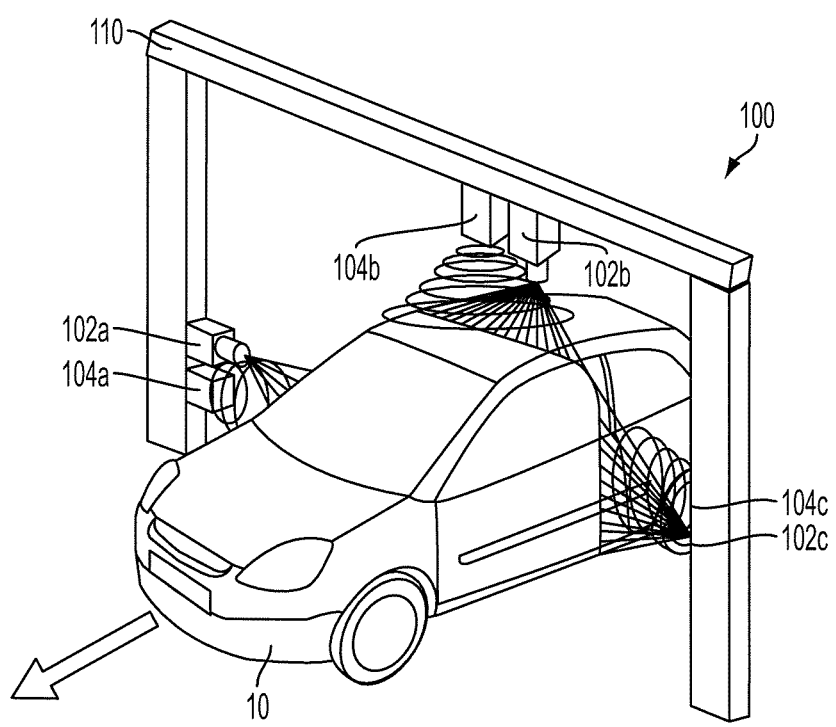
FIG. 1 is a schematic representation of an acoustic inspection system in accordance with exemplary embodiments of the invention.

FIG. 1 shows a system 100 for interrogating a vehicle 10 with acoustic energy of sufficiently low frequency to penetrate the surface of a container, such as a vehicle, and detecting the acoustic energy from the vehicle and vehicle contents to identify objects of interest. As used herein, identify means to characterize, detect, classify and/or identify the object. At least one low frequency acoustic source 102 having a selected frequency is arranged across an inspection area. At least one sensor 104 receives acoustic energy from the low frequency acoustic source 102 via the vehicle 10. In one particular embodiment, the inspection system 100 includes a frame 110 to support a sound source 102 to emit acoustic energy for ensonification of the vehicle, a first sensor 104a on the frame adapted for being located over the vehicle and second and third sensors 104b,c on respective sides of the frame to detect energy from sides of the vehicle. In the illustrated embodiment, first, second, and third acoustic energy sources 102a, b, c and first, second, and third sensors 104a, b, c, are shown.

As used herein, ensonify means to at least partially fill the interior of a container with acoustic energy. The acoustic responses of objects within the ensonified container can be measured and analyzed to detect, identify and localize the objects within the container.

Exemplary embodiments of the acoustic inspection system 100 enable monitoring of human trafficking and contraband without impeding the flow of commerce. Without the need to contact vehicles and with rapid measurement time, the inventive system allows vehicle inspection without stopping or opening the vehicle 10. In exemplary embodiments, inspections can take place at normal traffic speeds. Acoustic inspection of vehicles for concealed humans and contraband is achieved without creating traffic congestion or provoking tensions at border crossings and other security checkpoints.

It is understood that any practical number of acoustic energy sources 102 and sensors 104 can be used to meet the needs of a particular application. It is further understood that the sources 102 and sensors 104 can be located at various locations to ensonify particular vehicle types, such as small vehicles, e.g., motorcycles and smart cars, and large vehicles, e.g., trucks, construction equipment, and storage containers, and detect energy from the vehicles in a suitable manner. It is further understood that while exemplary embodiments of the invention are shown and described in conjunction with security checkpoints for vehicles, it is understood that embodiments of the invention are useful for detecting a wide variety of objects for an infinite number of applications. Exemplary inspection applications include bridge and tunnel security, bridge, tunnel and building structural inspection, monitoring the ingress and egress of vehicles from prisons, power plants, stadium events, underground parking, schools and other sensitive areas, ad-hoc checkpoints to search for kidnapped children or escaped prisoners, and portable inspection of luggage and suspicious packages. It is understood that a container can comprise any structure defining a volume where acoustic energy can pass through at least a portion of outer walls of the structure to ensonify the interior. The container can comprise any suitable material with acceptable acoustic behavior. Another exemplary application includes the search for items of interest under clothing or within internal cavities of an individual. A wide variety of further acoustic inspection applications will be readily apparent to one of ordinary skill in the art.

It is further understood that a range of acoustic frequencies can be used. In general, low frequencies, e.g., between about 1 Hz and about 200 Hz, generally propagate into a vehicle with less than about 6 dB loss for a 90 dB acoustic source. Higher frequencies (e.g. up to 2500 Hz) can be utilized with correspondingly higher loss. It is understood that any practical frequency can be used to achieve a desired level of ensonification. In an exemplary embodiment additive white Gaussian noise with a range of about 1-2500 Hz was used to generate test data. In other embodiments, source types such weighted Gaussian noise (e.g. "pink" or "brown" noise) as well as chirps, pure tones or combinations of different frequency ranges may also be utilized.

Referring again to FIG. 1, as the vehicle 10 travels through the inspection system 100, pulses of penetrating low-frequency acoustic energy from the sources 104a-104c are directed at the vehicle 100. In one particular embodiment, pseudo-random noise is used continuously and is correlated with signal return to localize the signal in time.

In general, the acoustic source 102 ensonifies the vehicle 10 so that resultant acoustic vectors are sampled on the surface of the vehicle, e.g., the trunk lid, roof, etc., can be measured. As described further below, the detected acoustic signal can be processed to identify objects of interest within the vehicle from an acoustic signature.

Figure 1A:
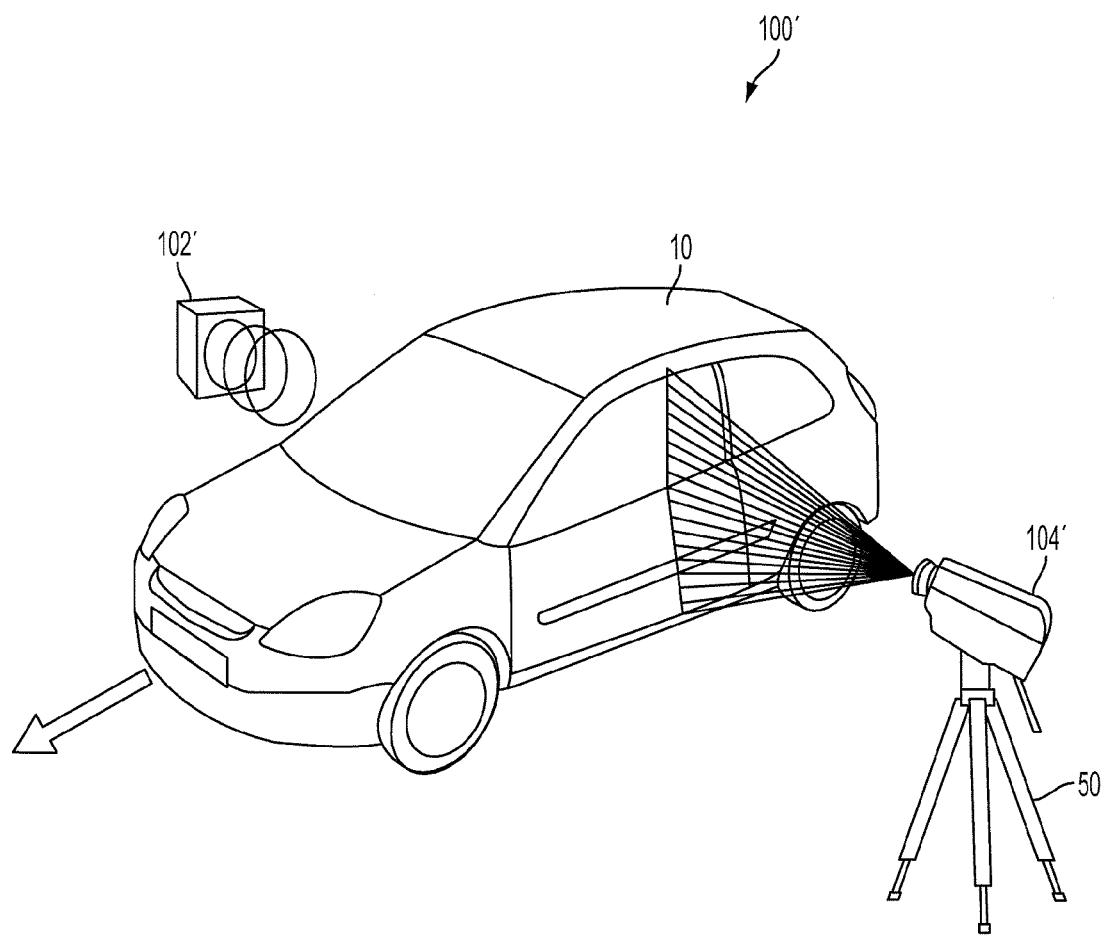
FIG. 1A is a schematic representation of an acoustic inspection system in accordance with exemplary embodiments of the invention.

In an alternative embodiment shown in FIG. 1A, a portable system 100' includes an acoustic energy source 102' to ensonify a vehicle. A sensor 104', which can be mounted on a tripod 50, detects acoustic energy on the surface of vehicle 10. It is understood that additional acoustic energy sources and sensors can be used, as shown in FIG. 1B.

The laser Doppler vibrometer 104 measures surface velocities as a function of displacements resulting from acoustic vibrations on the surface of the vehicle, e.g., the trunk, windshield, roof, etc. It is understood that the vibrations do not have to couple with the air to reach a remote detector as the laser Doppler vibrometer samples the container surface, as is well-known in the art. One type of laser Doppler vibrometer implements interferometry by measuring the interferometric bands produced when a reference beam is superimposed with a measurement beam to measure surface vibration. The beams are modulated by means of an acousto-optic modulator. Scattered light from the target is combined with light from the reference beam at a photo detector. The output of the photodetector is demodulated to derive the Doppler shift of the modulated frequency to determine the velocity versus time for the vibrations in a manner well known in the art.

While exemplary embodiments of the invention include a laser Doppler vibrometer, it is understood that any practical transducer, such as microphones, suitable to detect sound/vibrations on the ensonified target can be used.

It is understood that in exemplary embodiments of the invention, contact with the vehicle is not needed for inspection. Since the acoustic source and acoustic sensors do not require contact with the vehicle for inspection, the vehicle does not need to be stopped for acoustic interrogation. For example, in one embodiment, The vehicle travels through a "sampling field", wherein a 2 dimensional field of sampling points is projected by the vibrometer(s). As the vehicle passes through the field, the same point on the vehicle is re-sampled by the number of projected rows of sampling points. The spacing between rows can be adjusted as a function of vehicle speed in order to achieve the desired sampling rate. The vehicle may either be ensonified by an external source, or road noise may be used. In this way, the vehicle may be scanned at the desired sampling rate and resolution, while travelling at normal highway speeds.

Figure 2:
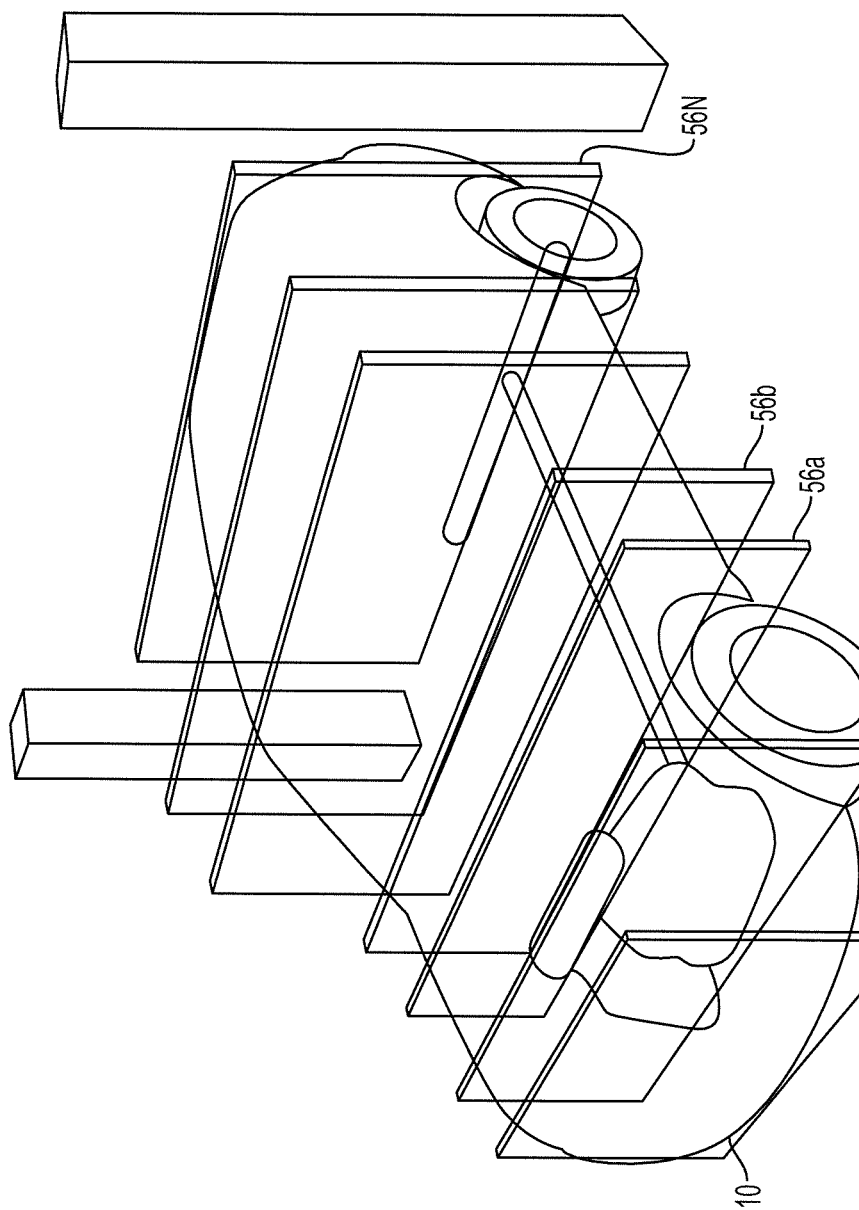
FIG. 2 is a pictorial representation of an acoustic inspection system using acoustic slices in accordance with exemplary embodiments of the invention.
Figure 3:
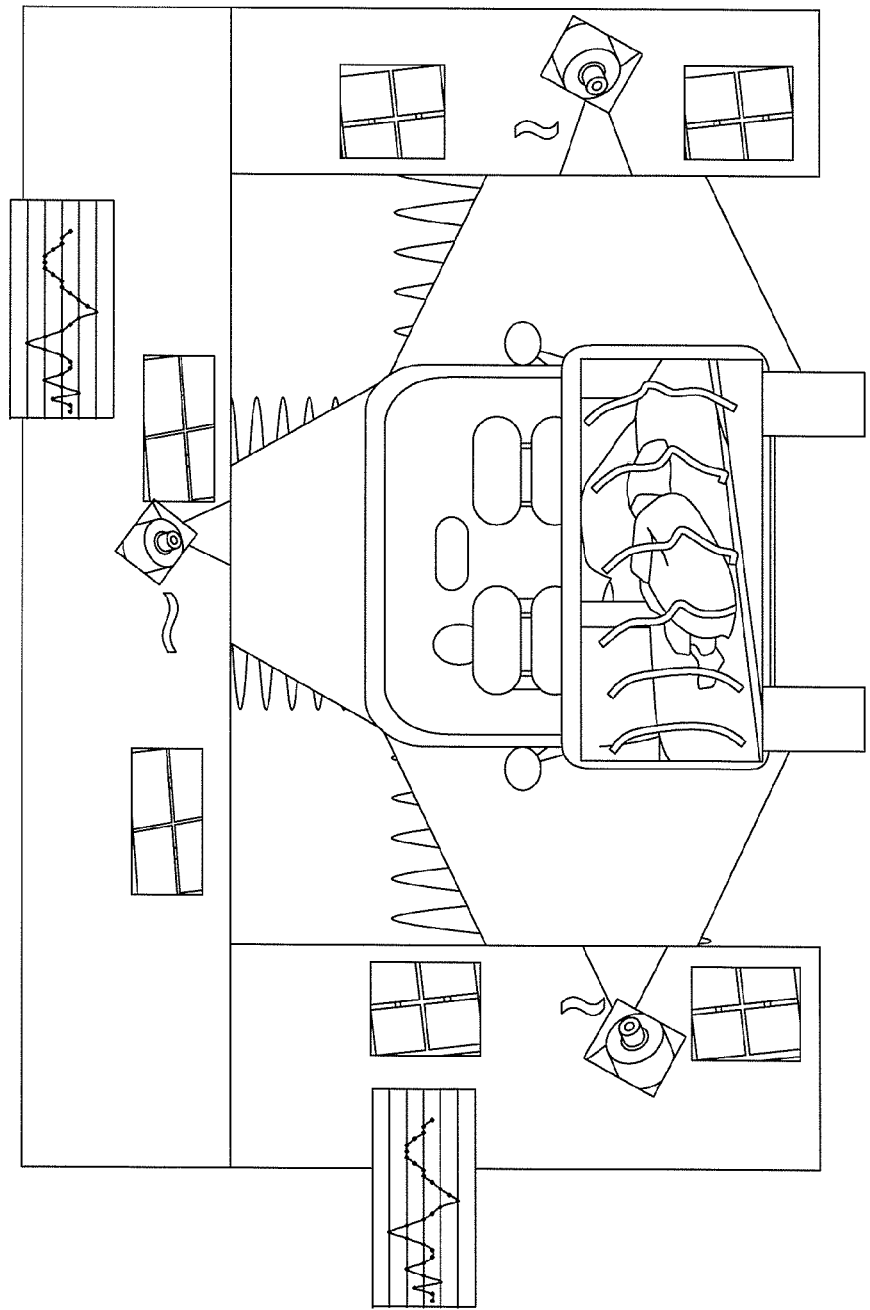
FIG. 3 is a pictorial representation of a back cut-away view of an inspected vehicle in accordance with exemplary embodiments of the invention.

As shown in FIG. 2, slices 1-$n$ can be taken of the vehicle 10 as it passes through the inspection system. This granularity can reveal unseen compartments and can locate humans hiding under seats or in the trunk, as shown in FIG. 3. It is understood that a desired slice resolution can be selected by adjusting the sampling field, source pulse rates, as well as the LDV scanning rate.

Figure 4:
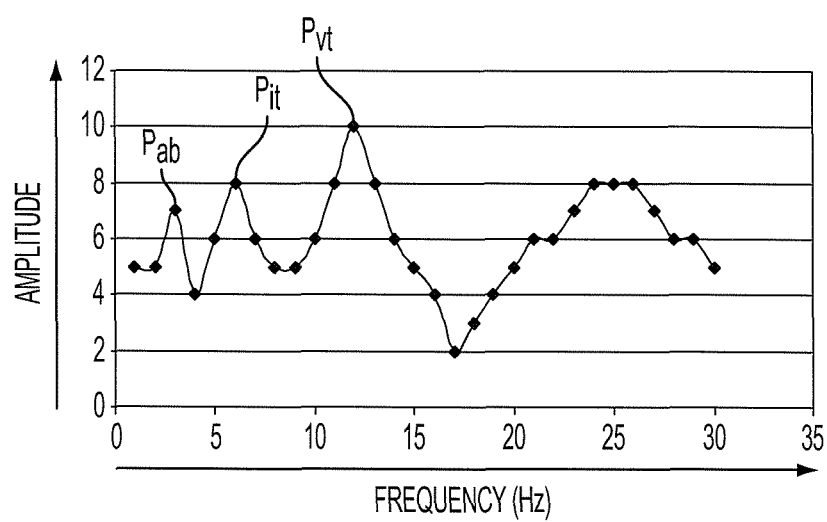
FIG. 4 shows a graphical representation of frequency versus amplitude with peaks corresponding to the resonant frequency for body structures.

In one aspect of the invention, exemplary embodiments are optimized to detect humans hidden in a vehicle. As described more fully below, cavities within a human body subjected to pulses from the acoustic sources penetrating the vehicle will resonate at specific frequencies, producing an acoustic profile characteristic of a human. Table 1 below shows an exemplary listing of resonant frequency values and body components. FIG. 4 shows a graphical representation of frequency versus amplitude with peaks P corresponding to the resonant frequency for the body structures in Table 1.

TABLE 1

| Resonant Frequency of Human Body Structures | |
|---|---|
| Hz | Body Structure |
| 3 | Abdomen |
| 5-7 | Lower torso |
| 10-14 | Upper torso |
| 20-30 | Head/shoulders |
| 60-90 | Eyes |

It is well-understood that different objects of interest will have different characteristic frequency and impedance profiles. Frequency-specific scattering and/or absorption of the acoustic energy reveals the general shape or extent of objects within the vehicle, either by reflection of scattered acoustic energy, or by shadowing due to absorption.

In an exemplary embodiment, a scanning laser vibrometer samples acoustic energy at the surface of a subject container (e.g. vehicle) in a grid, or other suitable pattern, to form a virtual microphone array. For a stationary vehicle, a two-dimensional grid scanning pattern provides the X and Y axes, and in the case of a moving vehicle, a one-dimensional vertical scan pattern provides the Y-axis, with the forward vehicle movement providing the X-axis.

In one embodiment, the resulting data array is converted into a frequency, or frequency-related domain in a manner well known in the art, such as by using the Fourier, Hilbert, Hilbert-Huang transforms, the wavelet, or wavelet packet transform directly to derive a frequency response, localized at the sampling point.

The data array can be processed as a virtual microphone array to facilitate beamforming to localize acoustic sources within a volume in a manner well known to one of ordinary skill in the art. It should be understood that beamforming may also be used to detect the shape an extent of an acoustic source, e.g. points marking the silhouette of a human body and/or acoustic scattering of features of the human body. Classification can be provided by classifiers, such as maximum likelihood estimation, support vector machines, and/or neural networks. In an exemplary embodiment, an automated system flags objects of interest as a function of possible location in the vehicle/container. For example, the system can ignore a detection of a human in the driver seat and flag a potential individual in the trunk, an engine compartment or under a dashboard.

Figure 5A:
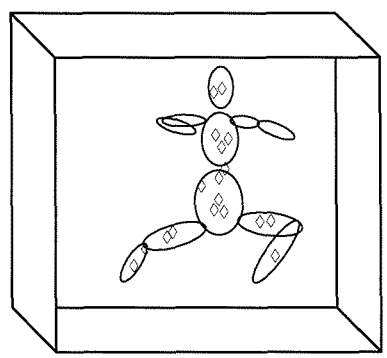
FIG. 5A is a body structure representation of a human.
Figure 5B:
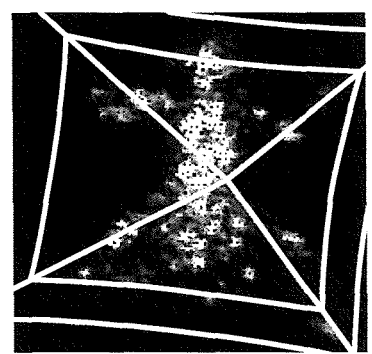
FIG. 5B is an image of the human of FIG. 5A derived from acoustical inspection.

FIG. 5A shows an exemplary body structure representation of a human in a given position and FIG. 5B shows an acoustically detected image for the human of FIG. 5A. As described more fully below, acoustic energy from the vehicle is processed to generate the image of FIG. 5B.

Figure 6:
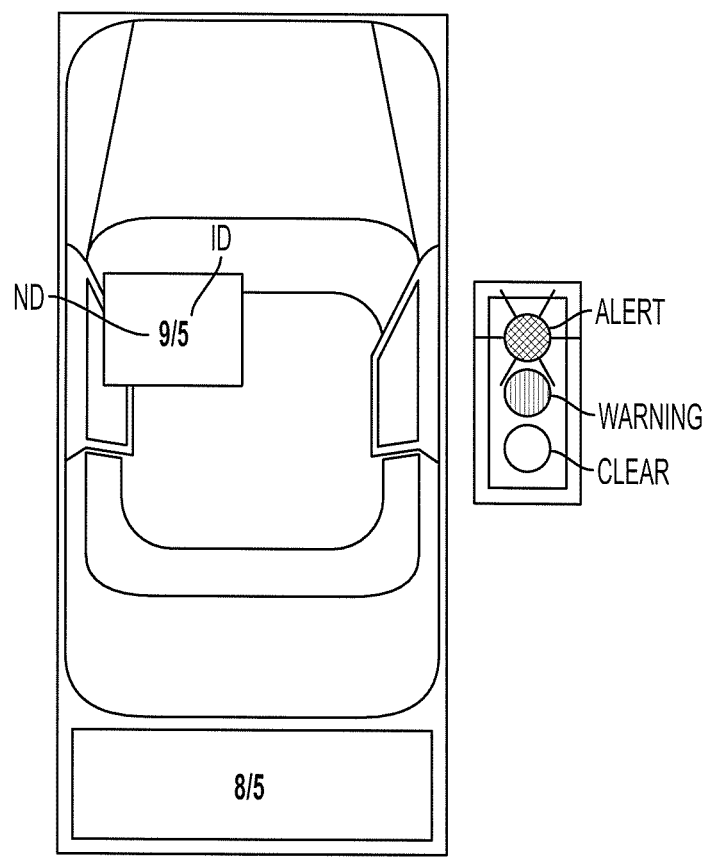
FIG. 6 is a schematic representation of an exemplary information display by an acoustical inspection system in accordance with the present invention.

FIG. 6 shows an exemplary display of a vehicle with a number of detections $N_D$ and intensity of detections $I_D$. The number of detections $N_D$ can be provided for a total number of items of interest. In another embodiment, the number of detections $N_D$ for particular items of interest can be provided. Items of interest for checkpoint applications can include humans, firearms, rocket propelled grenades, etc.

Figure 7:
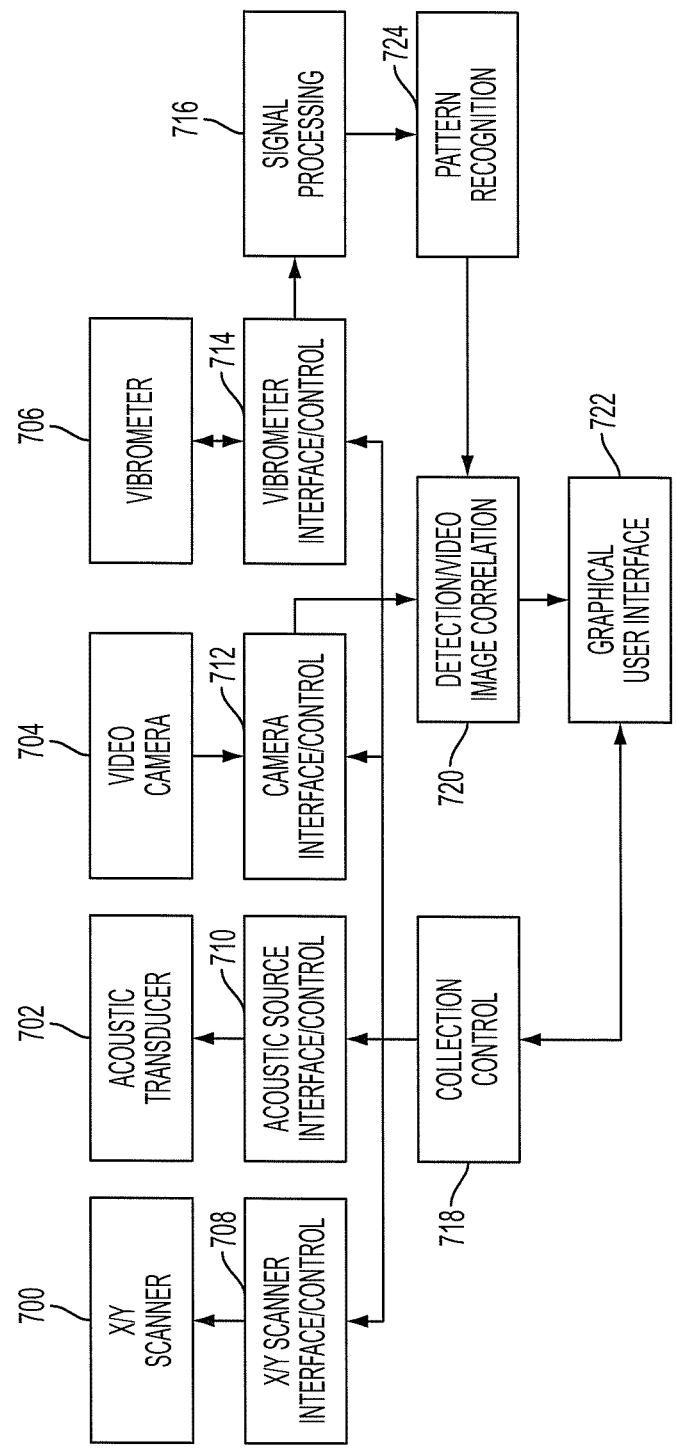
FIG. 7 is a schematic representation of an exemplary implementation for an acoustical inspection system in accordance with exemplary embodiments of the invention.

FIG. 7 shows further detail for an exemplary acoustic detection system in accordance with exemplary embodiments of the invention. In one embodiment, an X/Y Scanner 700 can include servomotors set at right angles having shafts attached to frontal surface mirrors. In another embodiment, a two-dimensional piezoelectric actuator is provided to which a single mirror is attached. It is understood that the frontal surface mirror is chosen so as to reflect the laser frequency used in the vibrometer 706 with a high efficiency, as is well known in the art. In another embodiment, the single sensor employed in the embodiments above may be replaced by an array of sensors, such as a CCD array, and the laser beam may be expanded to cover the entire sampled field. The laser power may be increased to provide the needed sampling energy. In this way, each point in the scan field may be sampled simultaneously, providing a high sample rate, real-time imaging capability.

The system can further include an optional acoustic transducer 702, such as a self-amplified low-frequency transducer, as is well known in the art. The system can also include an optional video camera 704. A camera interface/control 712 interfaces with and controls the camera 704 and receives and pre-processes video image data for the camera(s) 704.

In an exemplary embodiment, one or more suitable high resolution cameras, to which has been affixed either a suitable fixed or variable focal length lens. This lens may be either a fixed focus or auto-focus lens.

In an exemplary embodiment, the vibrometer 706 is provided as a laser Doppler vibrometer. The number of vibrometers is determined by the intended application along with the number of X/Y scanners 700. An X/Y Scanner Interface/Control 708 controls positional data sent to the X/Y scanner 700. A vibrometer interface/control 714 interfaces with and receives data from the laser vibrometer 706. In another embodiment a 3-dimensional laser Doppler vibrometer may be used to implement a tensor sensor. In an exemplary embodiment, a laser vibrometer device is defined as a member of a family of laser interferometric devices that measure displacement as a function of time, velocity, etc.

An acoustic source interface/control 710 interfaces with the acoustic transducer 702 to control signals sent to acoustic transducer 702. In one embodiment, the acoustic source provides additive Gaussian white noise. In another embodiment, acoustic 'chirps' are provided. It is understood that any practical acoustic source scheme can be used to meet the needs of a particular application.

A signal processing module 716 processes data received from the vibrometer interface 716. In an exemplary embodiment, processing includes a wavelet transform, Fourier transform, Hilbert Transform, Hilbert-Huang Transform and/or beam forming. A collection control 718 coordinates the interfaces 708, 710, 712, 714 to collect data from one or more scanning laser vibrometers 706 and video cameras 704. A video image/detection registration/correlation module 720 registers, e.g., overlays detection(s)/pattern(s) generated by processing module 716 with video image(s) generated by the camera 704. A pattern recognition module 724 recognizes patterns of objects of interest based on acoustic response, shape and/or extent, and fuses recognition data with acoustic images. A graphical user interface (GUI) 722 allows a user to control operation and view data and results from system.

Figure 8:
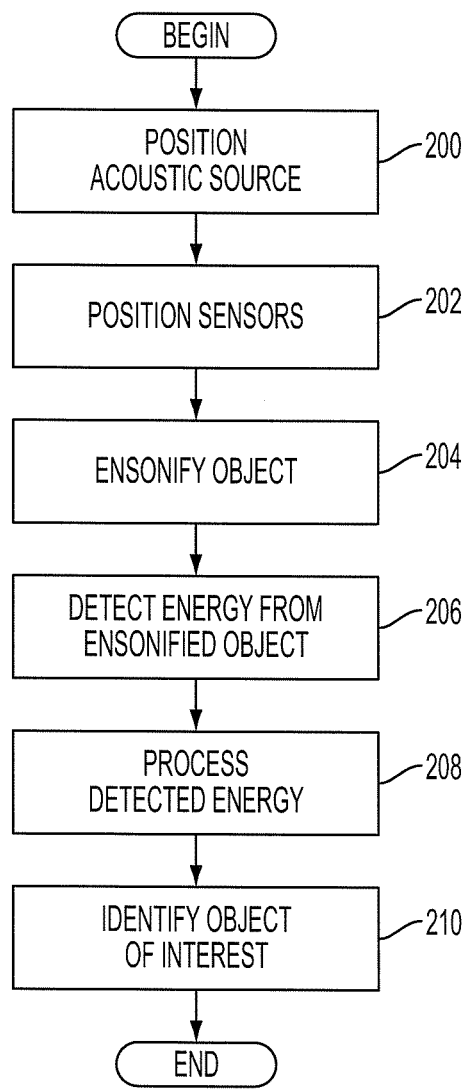
FIG. 8 is a flow diagram showing an exemplary sequence of steps for an acoustical inspection system in accordance with exemplary embodiments of the invention.

FIG. 8 is a flow diagram showing an exemplary sequence of steps for implementing acoustic inspection in accordance with the present invention. In step 200, at least one low frequency acoustic source is positioned to ensonify an object of interest, such as a vehicle. It should be noted that road noise could be exploited as an acoustic source. In one embodiment, "rumbler strips" could be employed. In step 202, at least one sensor is positioned to detect energy from the ensonified object. In one embodiment, the sensor is provided as a laser vibrometer to detect acoustic vectors on the surface of the ensonified object. The object is ensonified in step 204 by penetrating acoustic energy from the low frequency acoustic sources.

In step 206, vibrations on the surface of the ensonified vehicle are detected by one or more sensors, such as laser vibrometers. In step 208, the detected vibrations are processed to identify objects of interest in the vehicle or other container in step 210. Objects of interest include humans, contraband, firearms, explosives, and other items.

While exemplary embodiments of the invention do not require contact or stopping the vehicle or other object, it is understood that the inventive acoustic interrogation system can be used on a stationary object. For example, it may be desirable to use higher energy levels, longer sampling times or more aspects when passengers are not present in the vehicle.

Figure 9:
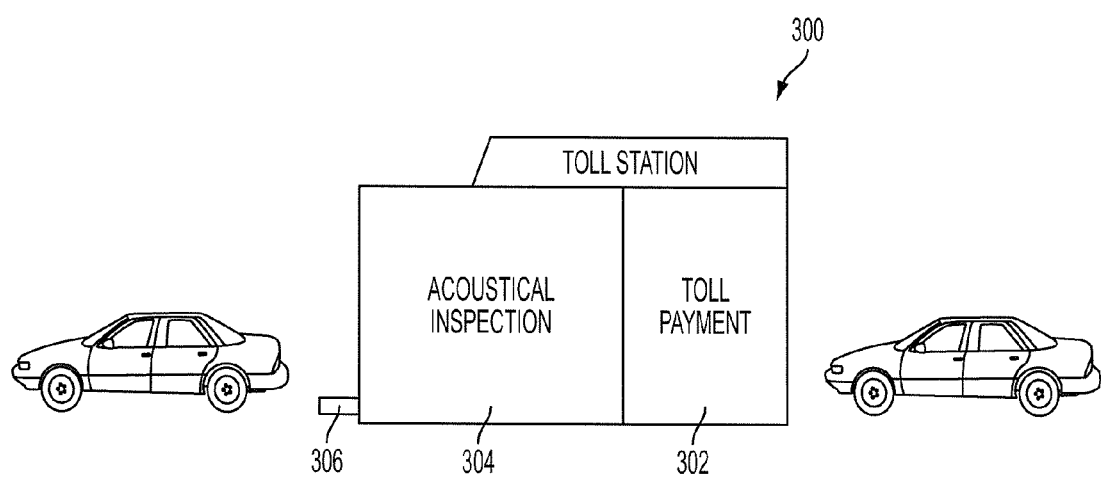
FIG. 9 is a schematic representation of a toll station including an acoustic inspection system.

In an exemplary embodiment shown in FIG. 9, a toll station 300 includes a toll payment system 302 and an acoustic detection system 304 in accordance with exemplary embodiments of the invention. It will be appreciated that the components of the acoustic detection system 304 can be readily integrated with a typical toll station. In one embodiment, one or more sensors 306 can also be positioned for detecting energy from a bottom of the vehicle. For example, sensors can be embedded in the road, in rumble strips, and the like.

Moreover, regular ensonification of vehicle occupants is not known to have any deleterious effects. The interrogating beams of acoustic energy can be unobtrusive, indistinguishable from road noise (except for certain overtones at certain power levels), and invisible.

It is understood that exemplary embodiments of the invention utilize ensonification to overcome acoustic impedance mismatches between open air and air in a contained area to be inspected by exploiting the fact that impedance is inversely related to frequency. Exemplary embodiments of the invention to penetrate auto interiors utilize Gaussian noise up to 500 Hz is used. Further embodiments can utilize higher frequencies, such as up to about 2500 Hz with somewhat higher losses. It is also understood that the technique may be applied to other acoustic media, such as water.

In general, the frequency band should be relatively low to mitigate container impedance and/or exploit known container acoustic characteristics. In one embodiment, broadband energy refers to Additive Gaussian White Noise for a source signal with constant spectral density and Gaussian distribution. In another embodiment, frequency-weighted (so-called 'colored') noise is used. Frequency chirps and tonal combinations can also be used in further embodiments to achieve greater efficiency for a particular container. In an alternative embodiment, a chord of tones, where the chord of tones corresponds to combinations of frequencies, or bands of frequencies, of interest for particular object searches, e.g., for human bodies, can be used to exploit container acoustic response characteristics. For example, a 'chirp' of ascending or descending tones, combination of tones, and/or band-limited broadband energy, can be used to meet the needs of a particular application.

In one embodiment, an acoustic inspection system includes an array of parametric sources. A parametric array is a transducer, such as acoustic source 102a in FIG. 1, generating an ultrasonic carrier wave, which is modulated with signal information. This approach enables ultrasonic energy to be transmitted as an acoustic beam, which remains tightly focused over a significant distance, e.g. 100 Meters. When this ultrasonic beam impinges upon a surface, such as a vehicle surface, the content is demodulated and becomes audible. Emitter array elements are focused on to a single point on the surface of the object of interest, thereby increasing their effective output by the use of constructive interference. As the ultrasonic energy is demodulated at the container surface, it is effectively coupled at that point. The resulting energy is of a sufficiently high level to penetrate the vehicle in quantities useful for detection.

Acoustic impedance mismatch is a well-known phenomenon that attenuates the propagation of a signal due to differences in the acoustic properties of adjacent media which reflect, rather than transduce the acoustic energy. Conventional acoustic-based interrogation techniques require direct coupling of a detector, either a microphone or accelerometer. Such approaches require setup time and a cooperative subject container.

As is known in the art, laser vibrometry operates by sampling surface displacement to generate a data stream for processing. While the source of a low frequency emitter is poorly localized, the detected items of interest are well localized since the amplitude of the spectral signatures is a function of proximity to the detection points. With the use of multiple detectors, movement of the searched vehicle generates detections at different points and from different aspects that can be used for interpolation, beamforming, the use of the tensor sensor method described below and/or other localization techniques to determine the location of items of interest. Scanning of the interrogating laser(s) can also be used in combination with the detectors. These unique locations may then be counted to determine the vehicle occupancy, quantity of contraband, etc., as described more fully below.

In one embodiment, as a vehicle passes through the acoustic inspection system the acoustic sources sequentially ensonify the vehicle in a circular fashion so as to create a 'spiral' of ensonification and detection points, as shown in FIG. 1 for example.

In another embodiment, an acoustic inspection system is passive where environmental noise ensonifies the object and absorption, refraction and reflection spectra are detected, combined and analyzed. As is known in the art, moving vehicles generate low frequency energy from the undercarriages that is of sufficient level and frequency to penetrate the vehicle in quantities useful to enable detection.

It is understood that a variety of techniques can be used for target classification/detection. Exemplary classifier mechanisms include neural networks, maximum likelihood estimation, support vector machine, etc. In one embodiment, a 'supervised' classifier 'learns' items of interest by 'training' on known examples of the items in order to learn how to associate the data and the class—e.g., frequency data associated with a human detection. These systems are then presented with and recognize these patterns and provide probabilities of detection or confidence levels, depending on the technique. In other embodiments, unsupervised classifiers learn by grouping data to establish class clusters. The classifier is then presented with exemplary data, which is mapped such that it falls close to, or within the pre-established class clusters. Such techniques are well-known in the art and can be readily adapted to meet the needs of a particular application.

In another aspect of the invention, an enclosed volume is ensonified for imaging items of interest in the volume. It is understood that the enclosed volume can be any space defined by a surface that can be ensonified by acoustic energy. It is understood that as used herein, enclosed means any volume that is at least partially enclosed with a surface on which vibration can be measured. For example, an automobile can have an enclosed interior with an open window. In general, the enclosed volume is ensonified using at least one low frequency acoustic source. Acoustic signatures of items of interest can be detected using one of more acoustic sensors, such as a laser vibrometer, to acquire the acoustic energy from the enclosed volume for processing to identify the objects of interest.

Figure 10A:
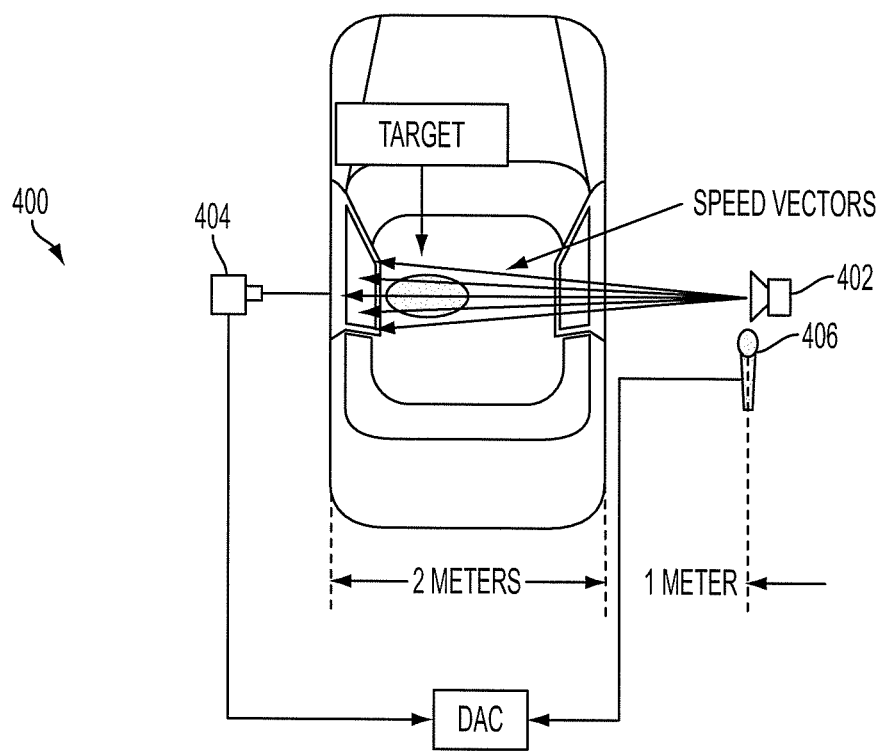
FIG. 10A is a schematic representation of an acoustic inspection system with first and second sensors in accordance with exemplary embodiments of the invention.

FIG. 10A shows an exemplary acoustic inspection system 400 using time difference of arrival (TDOA) information to localize an item of interest. The system 400 includes an acoustic energy source 402 and an acoustic sensor 404, such as a laser vibrometer 408. The system 400 also includes a microphone 406 proximate the acoustic energy source 402. A digital to analog converter (DAC) 410 is coupled to the vibrometer 408 and the microphone 406. In the illustrated embodiment for inspecting a vehicle 10 about two meters wide, the acoustic energy source 402 is about one meter from a side of the vehicle 10.

Figure 10B:
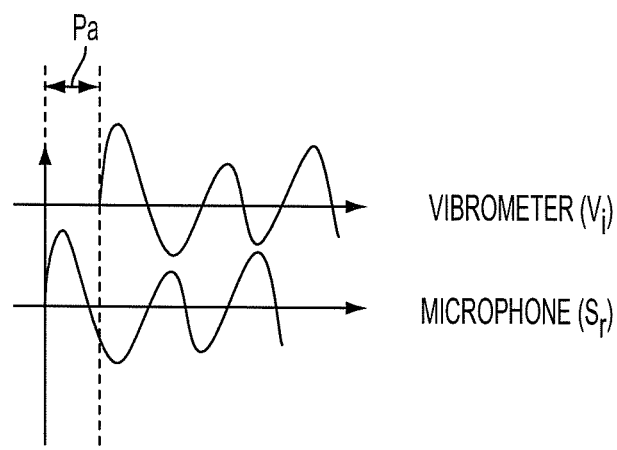
FIG. 10B is a graphical representation of respective signals at the first and second sensors for the exemplary system of FIG. 10A.

FIG. 10B shows a response 405 for the laser vibrometer and a response 407 for the microphone. As can be seen, the responses 405, 407 are similar with a time difference $P_d$ between the responses. In the illustrated embodiment, the vibrometer response 405 lags the microphone response by time $P_d$.

The time lag $P_d$ is due to the different propagation speeds in different media. The laser vibrometer 404 detects surface vibrations on the vehicle 10 by using lasers, e.g., light, while the microphone 406 detects sound traveling through air. The speed of sound in air is about 343 m/s and the speed of sound through soft human tissue is about 1540 m/s. It is understood that the microphone 406 and the laser vibrometer 404 are both connected to a common time source to enable accurate determination of the propagation time. Since the start time is known (from the microphone), and the arrival time (when sampled by the laser vibrometer) is known, the difference in time can be calculated. Pseudo-random noise could also be used to track a particular sample from generation to detection in order to infer propagation time.

Figure 11:
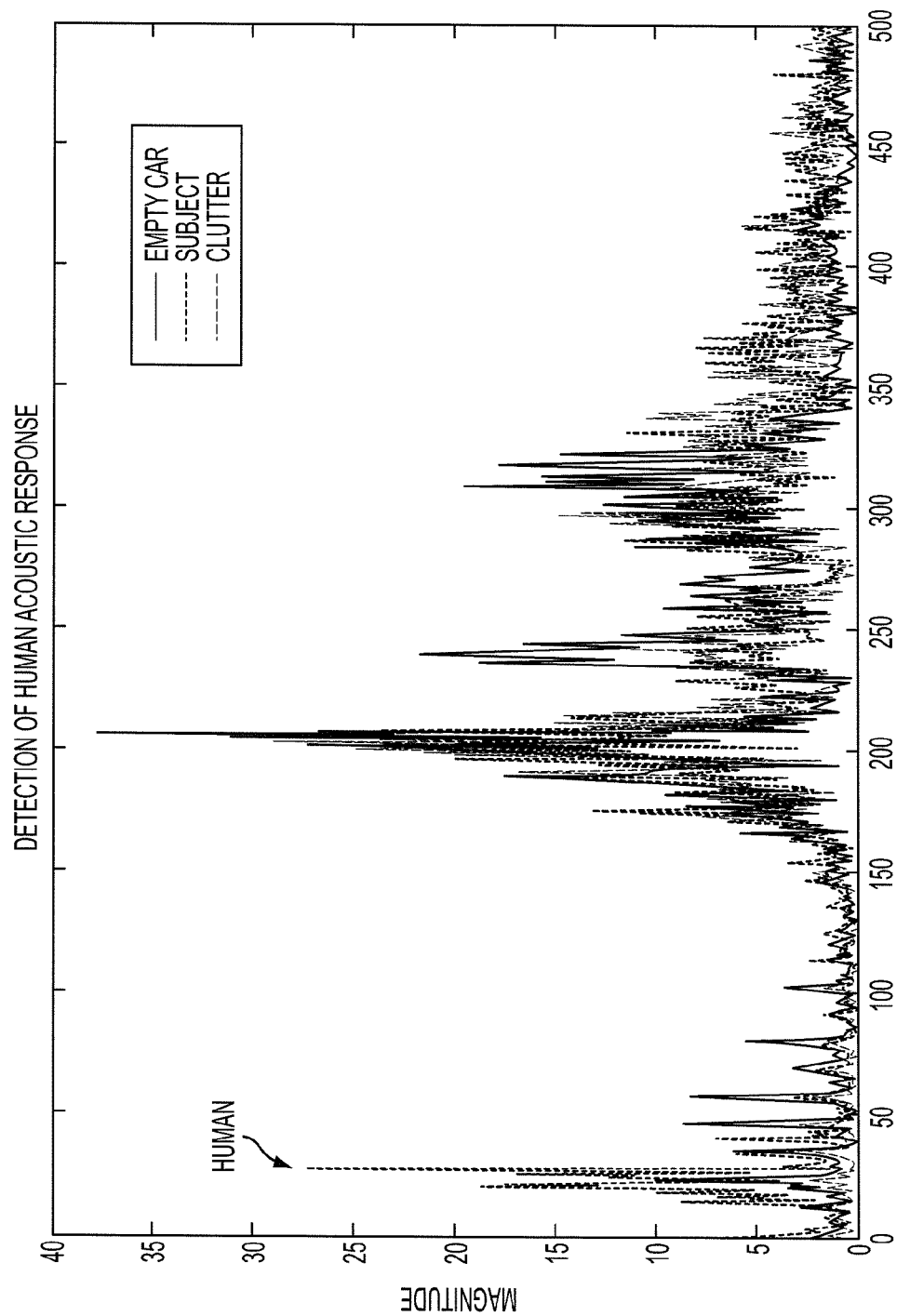
FIG. 11 is a graphical representation of a human acoustic response, an empty vehicle, and clutter.

FIG. 11 shows acoustic signatures for an empty automobile 450, clutter 452, and a human 454. FIGS. 12A-E show information for a vehicle and a human inside the vehicle in various locations detected by an acoustic sensor for the system of FIG. 10A in which the acoustic source is on the passenger side of the vehicle and the laser vibrometer is on the driver side of the vehicle.

FIG. 12A shows acoustic signatures for the (empty) vehicle 480a and a vehicle with a driver 482a, FIG. 12B shows acoustic signatures for the vehicle 480a and a vehicle with a human in the passenger seat 482b, FIG. 12C shows acoustic signatures for the vehicle 480a and a vehicle with a passenger in the rear driver side 482c, FIG. 12D shows acoustic signatures for the vehicle 480a and the vehicle with a human in the rear passenger seat 482d, and FIG. 12E shows acoustic signatures for the vehicle 480a and the vehicle with a human across the back seat 482e. As can be seen, the response magnitude is a function of proximity to the vibrometer laser spot location.

In exemplary embodiments of the invention, shape, extent, imaging and localization for a detected item of interest can be determined. In general, an enclosed volume, such as a vehicle, is ensonified by one or more acoustic sources and one or more acoustic sensors detects the acoustic signature of the item of interest. Data can be collected on points in a grid forming a part of the volume surface, as described more fully below.

FIGS. 13A-E show acoustic data sampled at grid points and processed. FIG. 13A shows acoustic data sampled, such as by the system of FIG. 10A, for a grid. As can be seen, a human acoustic response is present in the sampled grid data. In this example, the grid is 11 inches by 32 inches with 352 grid points, where each cell is one inch by one inch. The sampled data is from a vehicle with a driver present. FIG. 13B shows grid data at 20 Hz and FIG. 13C shows grid data at 9 Hz. As can be seen, there is significant response in the human acoustic response about 9 Hz. FIG. 13D shows a picture corresponding to the grid. FIG. 13E shows a video image overlaid with the grid data.

Figure 13F:
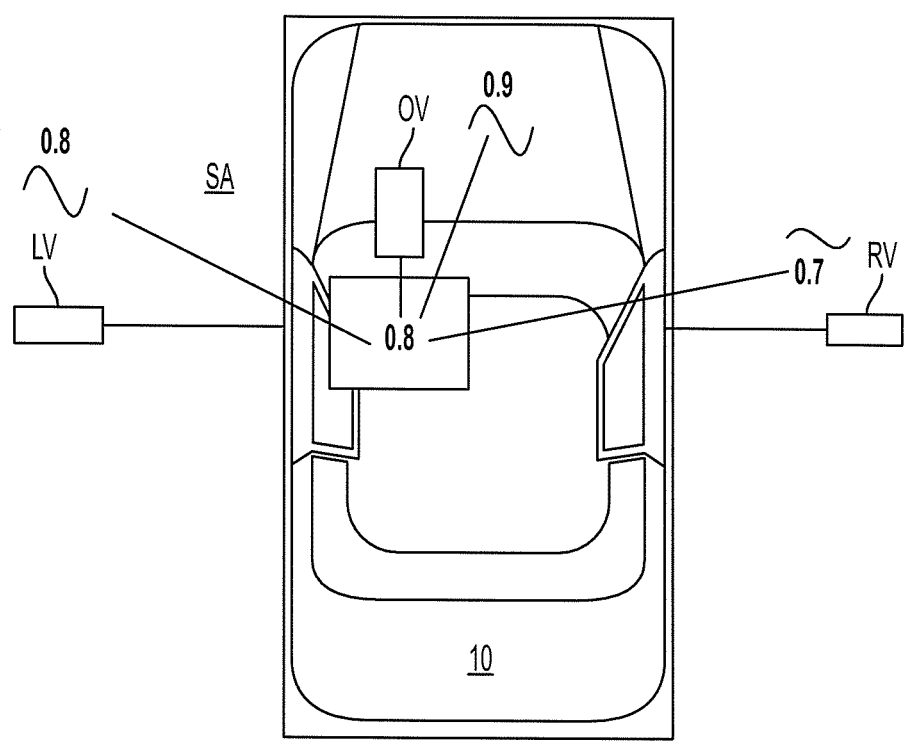
FIG. 13F shows an acoustic response for various sensor locations to provide interpolation of item location.

In one embodiment, interpolation based localization is performed. Displacement frequency data is derived from the vibrometer velocity data, as shown in FIG. 13F. The system integrates the power spectral density over the human response acoustic sub band, such as the human response shown in FIG. 11. For example, the human acoustic sub band can be selectable from about 2 Hz to about 50 Hz. Data points can be interpolated to find energy peaks, which can represent a location of the object of interest. By processing the vibrometer data, the extent, shape, and location of items of interest can be determined.

FIG. 13F shows exemplary localization of an item of interest, such as a human, within a vehicle using an acoustic inspection system in accordance with exemplary embodiments of the invention. As the vehicle 10 travels through a sensor array SA, which can include any number of vibrometers, a set of normalized magnitude values for the frequency spectrum of interest is calculated on periodic or other time interval. The magnitude of the values is a function of how close the item of interest is to the surface of the vehicle being monitored by the vibrometer(s). The location of the human in the vehicle can be determined by interpolating the measured values. For example, if a first vibrometer LV off the left (driver) side of the vehicle returns a normalized value of 0.8, an overhead vibrometer OV returns a normalized value of 0.9, and a right (passenger) side vibrometer RV returns a value of 0.7, it can be determined that the human is located in the driver seat of the vehicle.

Figure 13G:
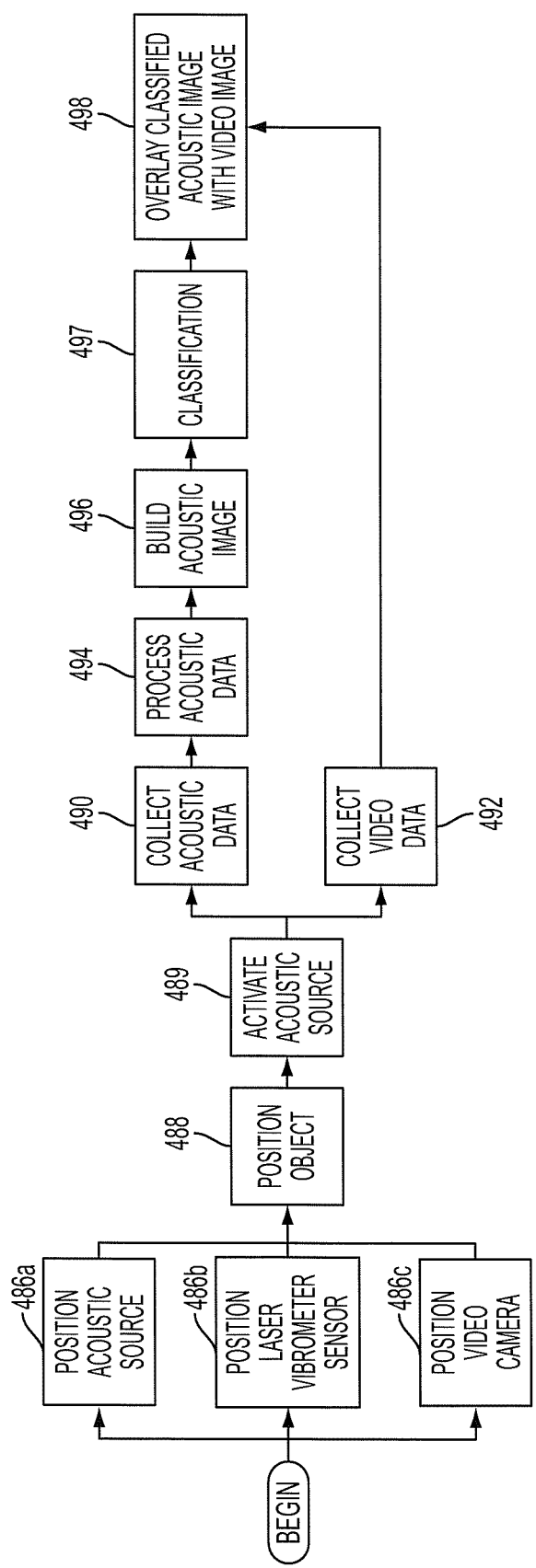
FIG. 13G is a block diagram of an exemplary acoustic inspection system with image comparison.

FIG. 13G shows an exemplary sequence of steps for implementing acoustic inspection and video image registration. In step 486, the acoustic source(s), the laser vibrometer (s), and the video camera(s) are positioned. In step 488, the object to be inspected, such as a vehicle, container or other enclosed volume, is positioned. It is understood that the object can be moving as it is positioned. In step 489, the acoustic source is activated to ensonify the object.

In step 490, acoustic data from the vibrometer is collected and in step 492, video data is collected. The acoustic data will typically be collected at the same time as the video data for a particular surface area. In step 494, the acoustic data is processed to generate an acoustic image in step 496. In step 497, the acoustic information is classified, and in step 498, the acoustic image is positionally overlaid with the video image. That is, the video image is registered with the acoustic image.

Figure 14C:
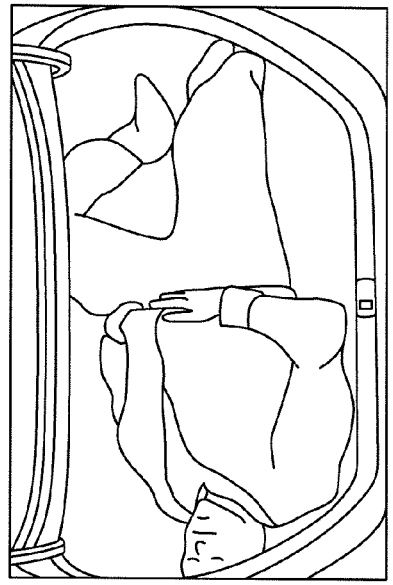
FIG. 14c is an image of a human in a vehicle.
Figure 14D:
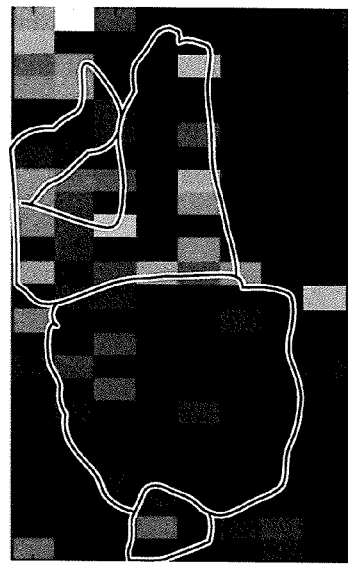
FIG. 14d is an overlay of acoustic data and video image.
Figure 14A:
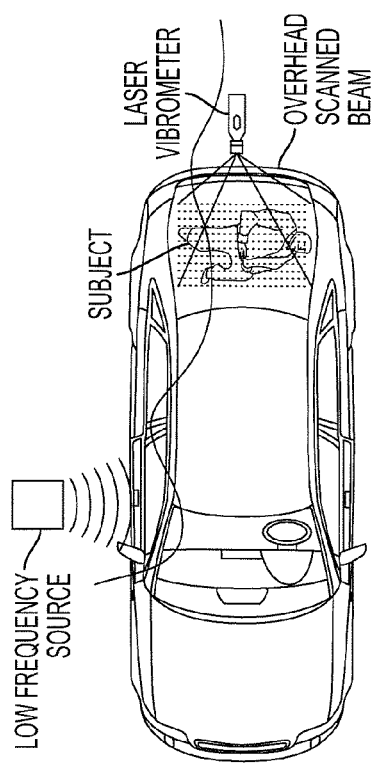
FIG. 14a is an exemplary acoustic inspection system.
Figure 14B:
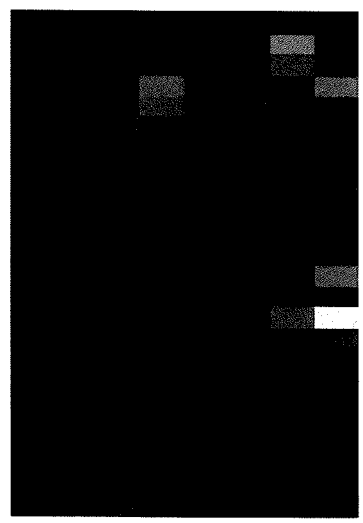
FIG. 14b is a representation of acoustic data.

FIG. 14A shows an exemplary acoustic inspection system 500 including a low frequency source and an overhead laser vibrometer to detect surface vibration on the trunk of an automobile. FIG. 14B shows grid data corresponding to an acoustic image of an empty trunk using the overhead vibrometer. FIG. 14C is an image of a human in the trunk of the vehicle. FIG. 14D is a grid data corresponding to the human in the trunk shown in FIG. 14C. FIG. 14D shows registration of the human with the grid data. It is understood that the grid data is relatively low resolution and that higher resolution will increase detection and imaging.

Figure 15A:
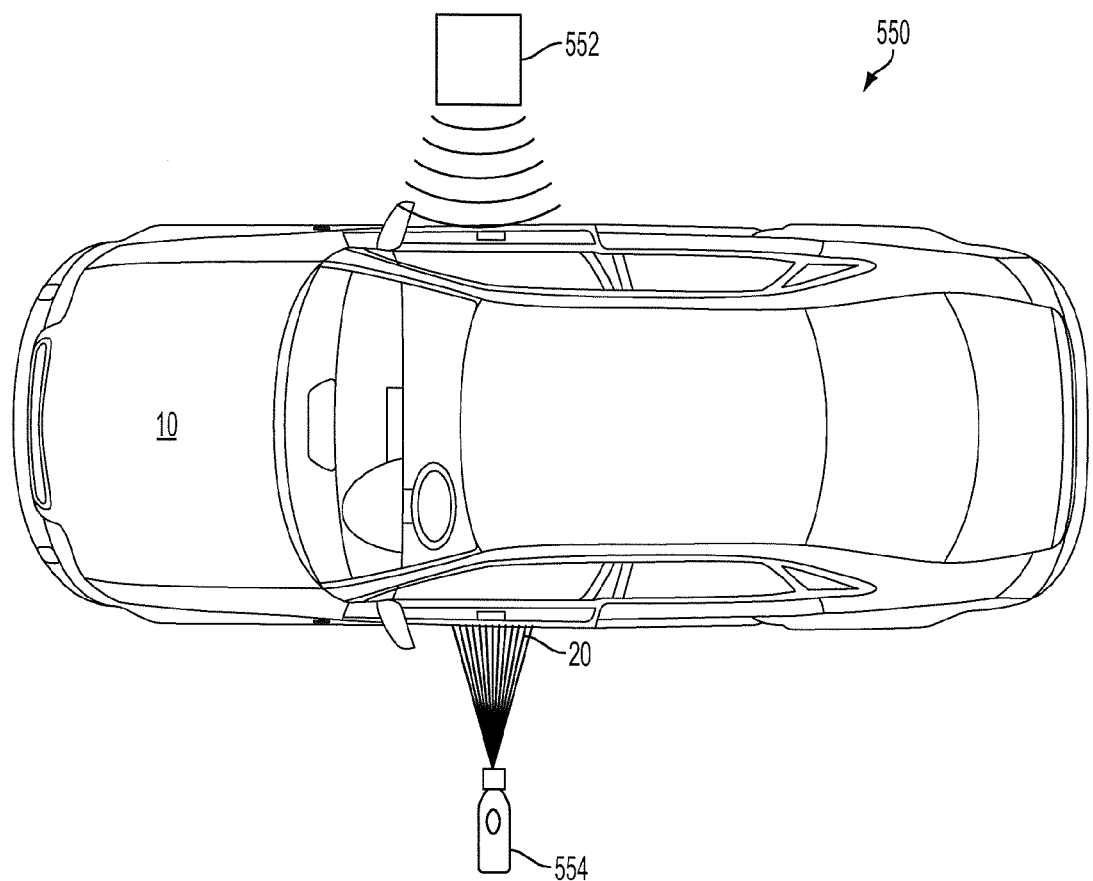
FIG. 15A is a schematic representation of an acoustic inspection system identifying an item of interest.
Figure 15B:
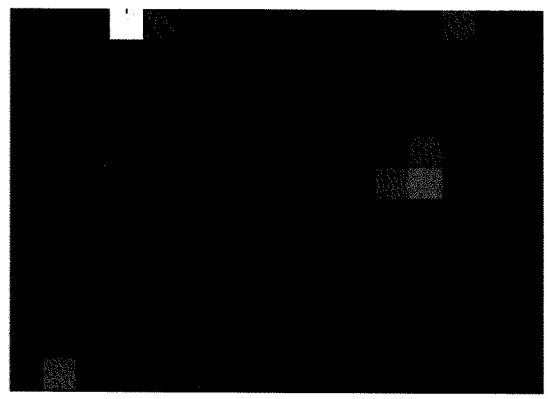
FIG. 15B shows acoustic data for the item in FIG. 15A.
Figure 15C:
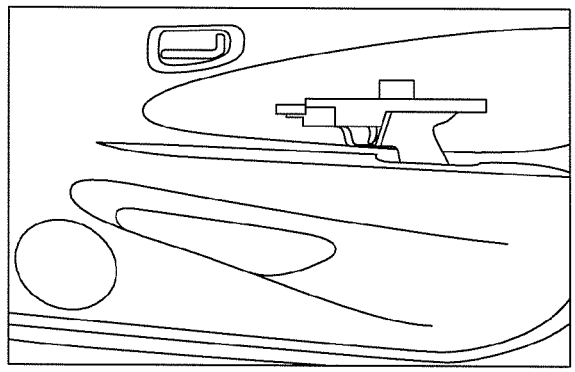
FIG. 15C is a photo of the item of FIG. 15A.
Figure 15D:
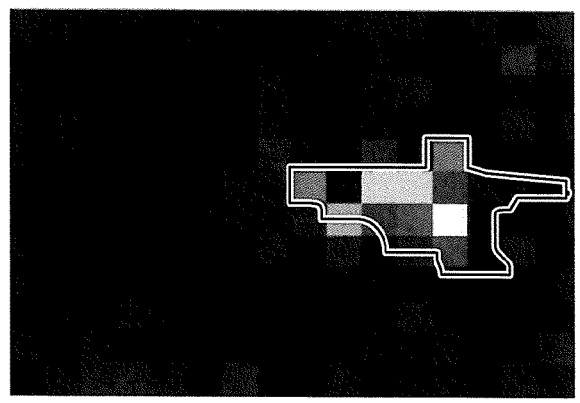
FIG. 15D is an overlay of the acoustic data and the photo image outline.
Figure 15E:
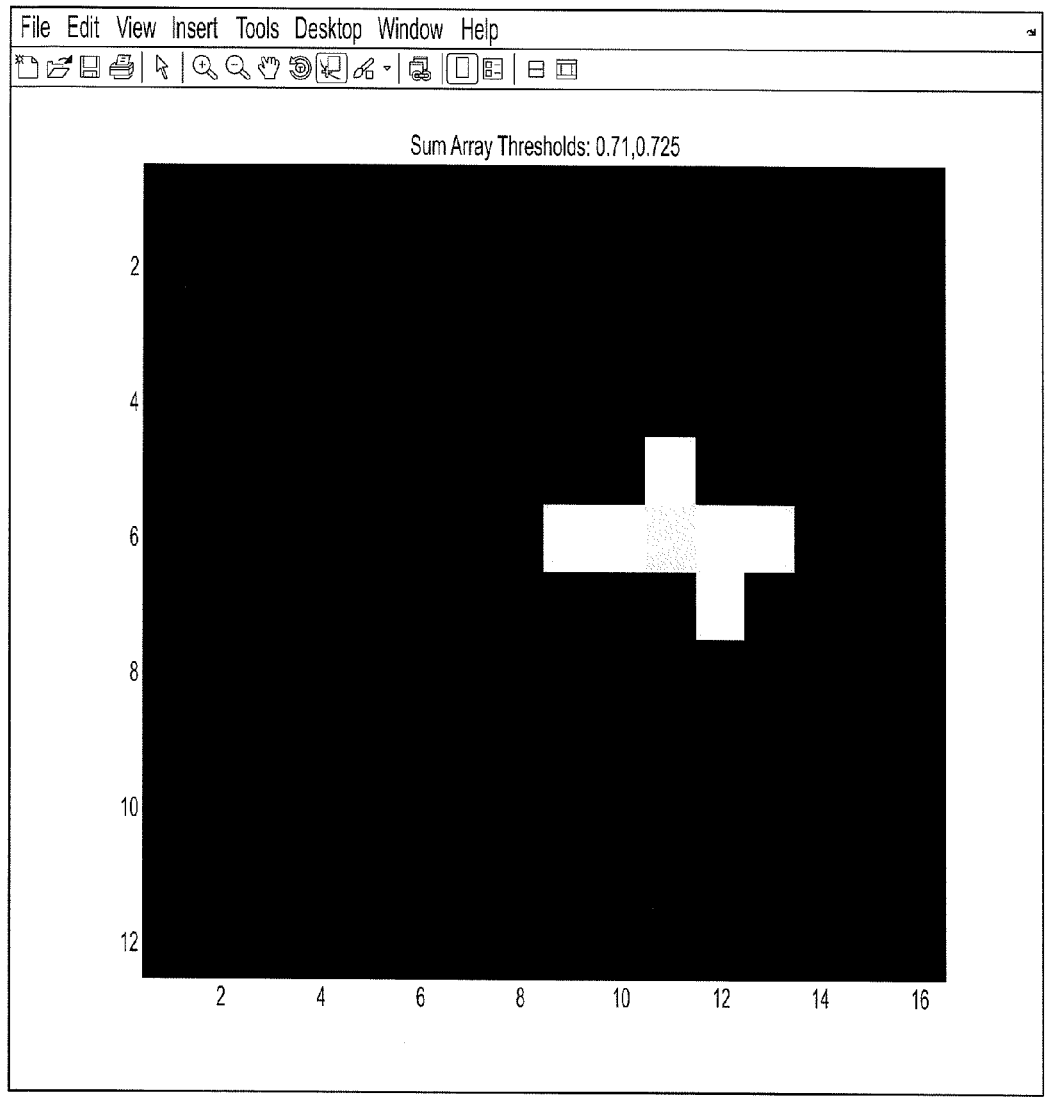
FIG. 15E is an acoustic image of a gun a car door after processing.

FIG. 15A shows an exemplary acoustic inspection system 550 including a low frequency source 552 directed at a passenger side of a vehicle 10 and a laser vibrometer 554 directed at a driver side of the vehicle. A handgun 20 is located on the inside of a driver side door of the vehicle. FIG. 15B shows an acoustic image/grid data for an empty car door. FIG. 15C shows a picture of the handgun 20 on the door. FIG. 15D shows an acoustic image of the handgun on the door and registration of the handgun in the picture and acoustic signature. The extent of the handgun 20 is clearly visible in the acoustic image. FIG. 15E is an acoustic image of a gun in a car door after post processing. FIG. 15G shows more detail for a post processed acoustic image of a gun.

Figure 15F:
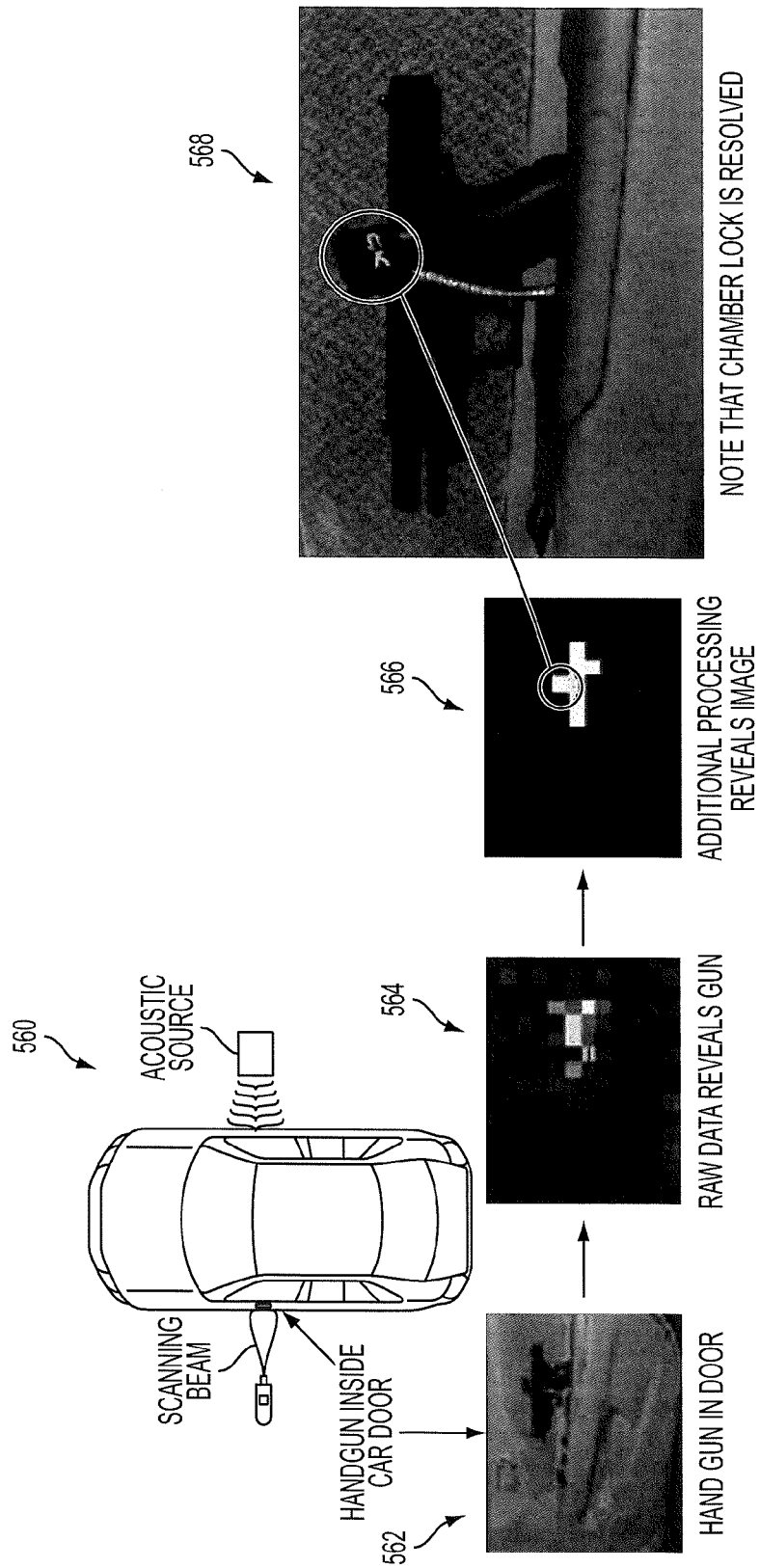
FIG. 15F is a schematic representation of acoustic inspection system interrogating a vehicle with a hand gun in the door.
Figure 15G:
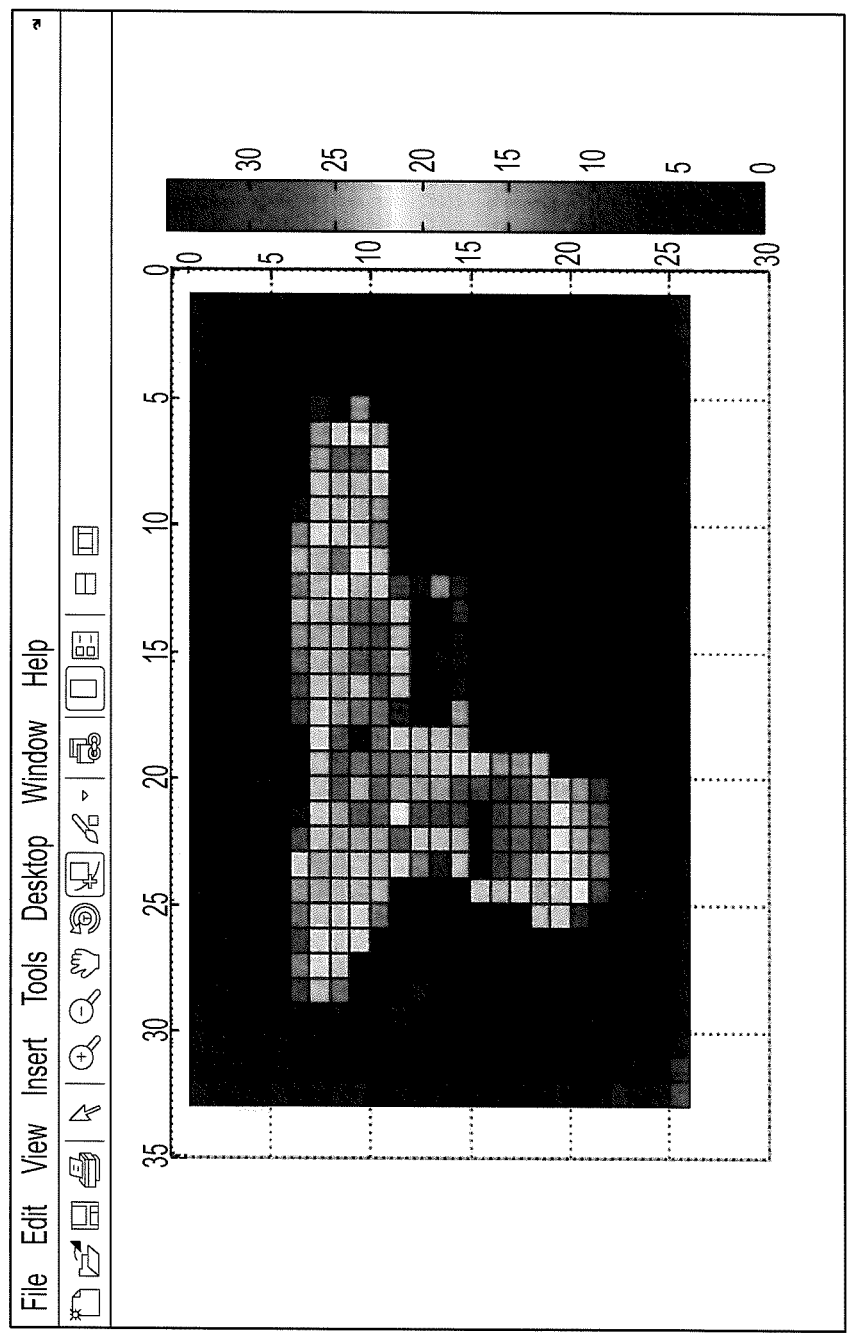
FIG. 15G shows more detail for a processed acoustic image of a gun.
Figure 15H:
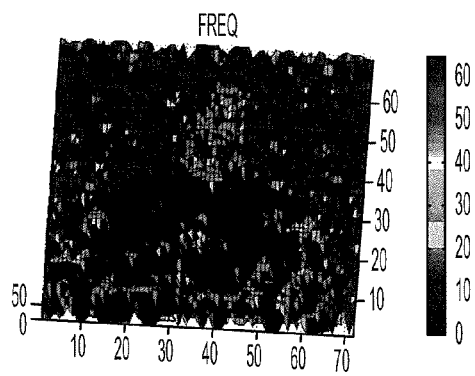
FIGS. 15H-K shows acoustic images of a human head and torso.
Figure 15I:
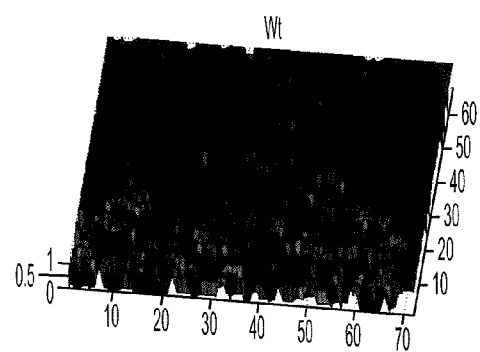
Figure 15J:
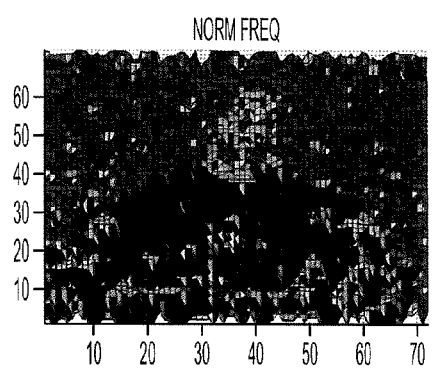
Figure 15K:
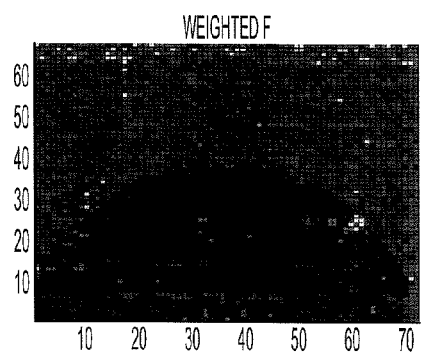

FIG. 15F shows an acoustic inspection system interrogating a vehicle with a hand gun in the door 562. Raw acoustic image data 564 reveals a gun and processed acoustic image data 564 reveals additional features of the gun, such as a chamber lock shown in the photograph 568 of the gun in the door.

FIGS. 15H-K show acoustic images of a human head and partial torso for frequencies between 1 Hz and 70 Hz. The head and torso are clearly discernible.

Figure 15L:
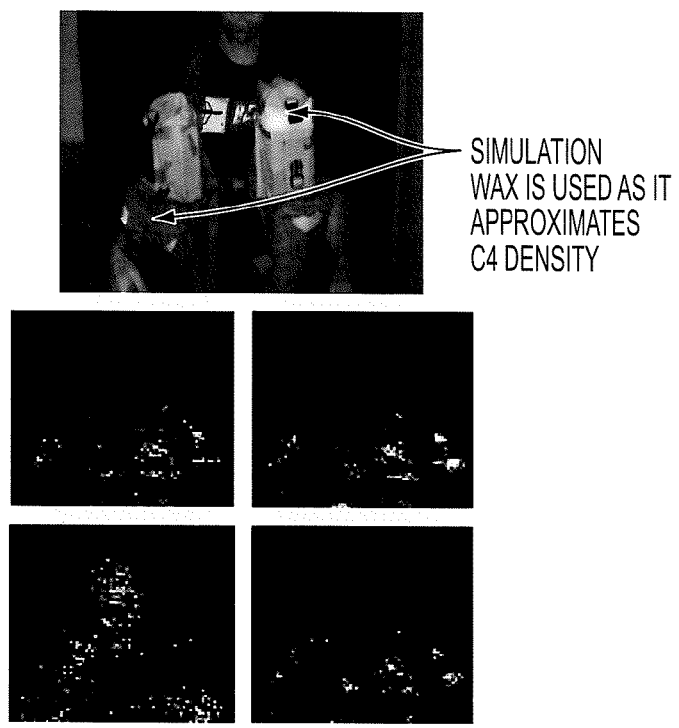
FIGS. 15L-M show a human with a simulated explosive material hidden under a jacket, raw acoustic image data (FIG. 15L) and processed data (FIG. 15M)
Figure 15M:
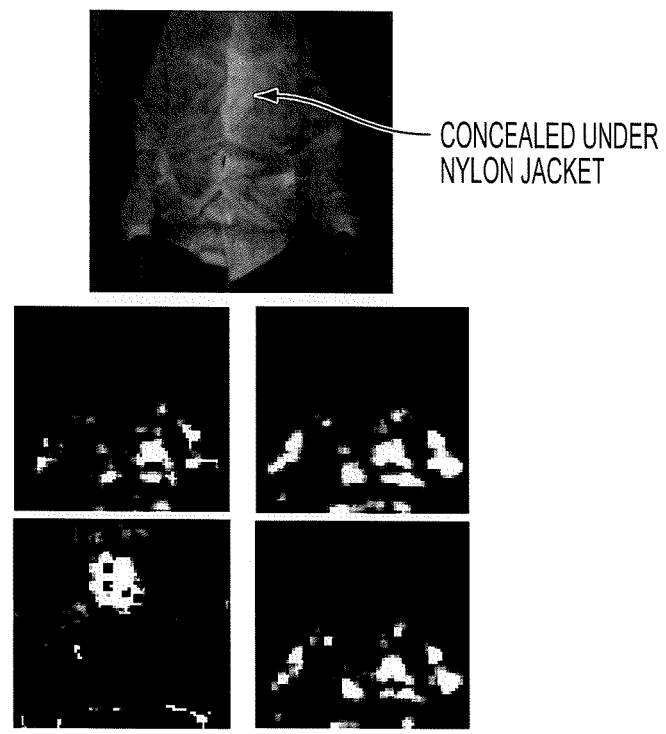

FIGS. 15L-M show a human with a simulated explosive material hidden, e.g., wax, under a jacket, raw acoustic image data (FIG. 15L) and processed data (FIG. 15M). The raw acoustic data is 70×74 cm with 1 cm resolution. As can be seen, features in the image respond at different frequencies. For example, the head, eyes, arms, vest/belt, and simulated explosive can be seen.

In another aspect of the invention, a system for detecting items of interest including integrating information from multiple sensors. In general, different types of sensors and information are integrated to reduce false alarms and increase the probability of detection of items of interest.

Figure 16:
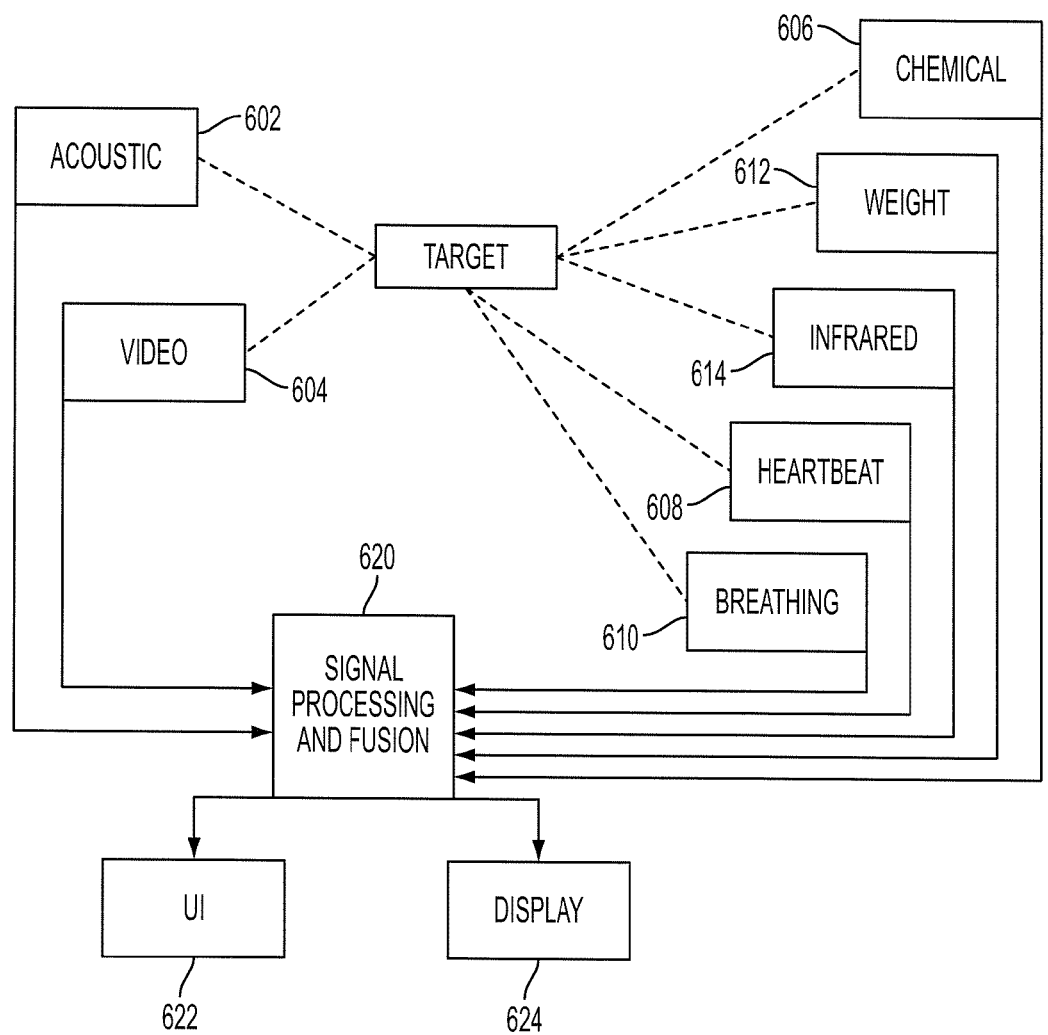
FIG. 16 is a block diagram of an inspection system having multiple sensors.

FIG. 16 shows an exemplary system 600 for detecting objects of interest within an enclosed volume. The system 600 includes an acoustic inspection system 602 and a further inspection system providing data that can be merged with the acoustic inspection system 602. In an exemplary embodiment, the system 600 includes a video system 604 to obtain images of the volume surface, for example. An image can be registered with an acoustic image, as described above.

The system can include any practical number and type of additional sensors. In one embodiment, the system includes a chemical sensor system 606 to detect the presence of certain chemicals, such as explosive residue, water vapor, humidity, etc. A heartbeat detection system 608 can detect the presence of heartbeats in a vehicle or other container. In one embodiment, a heartbeat detection system 608 detects a number of heartbeats that can be compared to what is observed, reported, or otherwise expected for number of heartbeats in the vehicle. If the number of heartbeats does not match the expected number of people in the vehicle, an alert can be generated. Heartbeat detection systems are well known the art. Similarly, a breathing detection system 610 can detect breathing for human in a vehicle or other container. A weight system 612 can weigh a vehicle to determine whether there is a deviation from an expected weight for the vehicle and the actual weight. In one embodiment, data from an infrared system 614 (e.g., an infrared imaging system) is used to detect a higher than normal heat signature emanating from a trunk, fused with acoustic and/or other evidence to indicate a subject in a trunk with a high degree of confidence than possible by relying on any single source.

Information from the sensor systems can be provided to a signal processing/fusion module 620, which can be coupled to a user interface 622 and display 624. The signal processing module/fusion module 620 can process the sensor data to reduce false alarms and increase the probability of detection. As described above, information from an acoustic inspection system 602 can be combined with information from a video system 604 to enhance detection of items of interest.

In general, information from the sensor systems can be combined in any practical manner to meet the needs of a particular system. In one embodiment, the system requires confirmation of a detected hidden human in a vehicle by the acoustic inspection system 602 by also requiring at least one of the heartbeat detection system 608 and the breathing detection system 610. For example, the acoustic inspection system 602 indicates three passengers in a vehicle, two of which are visually confirmed as driver and passenger. The third is indicated as being in the trunk. The heartbeat detection system 608 detects three heartbeats, which confirms three humans in the vehicle so that an alert can be generated. In this example, the breathing detection system 610 could provide confirmation of three humans if the heartbeat detection system did not identify three humans.

It is understood that components and processing for exemplary embodiments of the invention can be partitioned between hardware and software to meet the needs of a particular embodiment. For example, processing can be performed by instructions stored in a memory executing on a processor, as well as performed in various hardware components, such as Field Programmable Gate Arrays (FPGAs), and combinations thereof. Exemplary embodiments of the invention include a computer to implement acoustic inspection.

Figure 17:
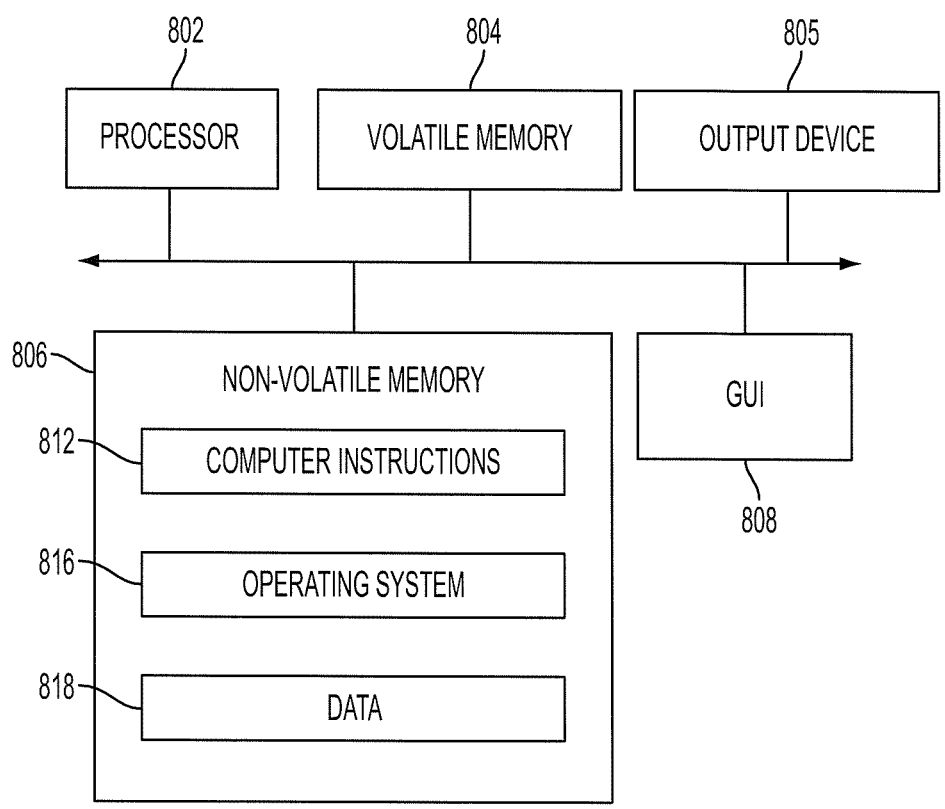
FIG. 17 is a block diagram of an exemplary computer system that can form a part of an inspection system embodiments.

FIG. 17 shows a computer including a processor 802, a volatile memory 804, a non-volatile memory 806 (e.g., hard disk), a graphical user interface (GUI) 808 (e.g., a mouse, a keyboard, a display, for example) and an output device 805. The non-volatile memory 806 stores computer instructions 812, an operating system 816 and data 818 including the Q files, for example. In one example, the computer instructions 812 are executed by the processor 802 out of volatile memory 804.

Processes are not limited to use with the hardware and software of FIG. 17; they may find applicability in any computing or processing environment and with any type of machine or set of machines that is capable of running a computer program. Processes may be implemented in hardware, software, or a combination of the two. Processes may be implemented in computer programs executed on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform process and to generate output information.

The system may be implemented, at least in part, via a computer program product, (e.g., in a machine-readable storage device), for execution by, or to control the operation of, data processing apparatus (e.g., a programmable processor, a computer, or multiple computers)). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer to perform processes. Processes may also be implemented as a machine-readable storage medium, configured with a computer program, where upon execution, instructions in the computer program cause the computer to operate in accordance with processes.

In exemplary embodiments, vector/tensor localization may be used to estimate the position, shape and extent of objects within a volume. Accurate shape and extent data complements frequency and other features to enhance system classification performance and/or imaging. Such systems require the X, Y and Z vector/tensor components of acoustic point-sources located on surfaces of items of interest located within the volumes of containers under inspection.

In one embodiment of such as system, a portable version which implements the vector/tensor localization algorithm utilizes a 3D scanning laser Doppler vibrometer, which may be used to scan either stationary or mobile targets. This system would be used where a single aspect scan would suffice.

In another embodiment, a vehicle screening portal system implementing the vector/tensor localization algorithm utilizes an array of 3D scanning laser Doppler vibrometers and acoustic transducers which would scan the vehicle from 3 aspects—i.e. left, right and overhead. Such a system may be used to scan stationary or moving vehicles. In an alternative embodiment, an array of 1D scanning laser Doppler vibrometer is used, which relies on vehicle motion to capture X, Y and Z vector components.

It is understood that such systems can be scaled to, for example, screen living subjects or packages. The below provides further detail of acoustic signal processing in accordance with exemplary embodiments of the invention.

Figure 18:
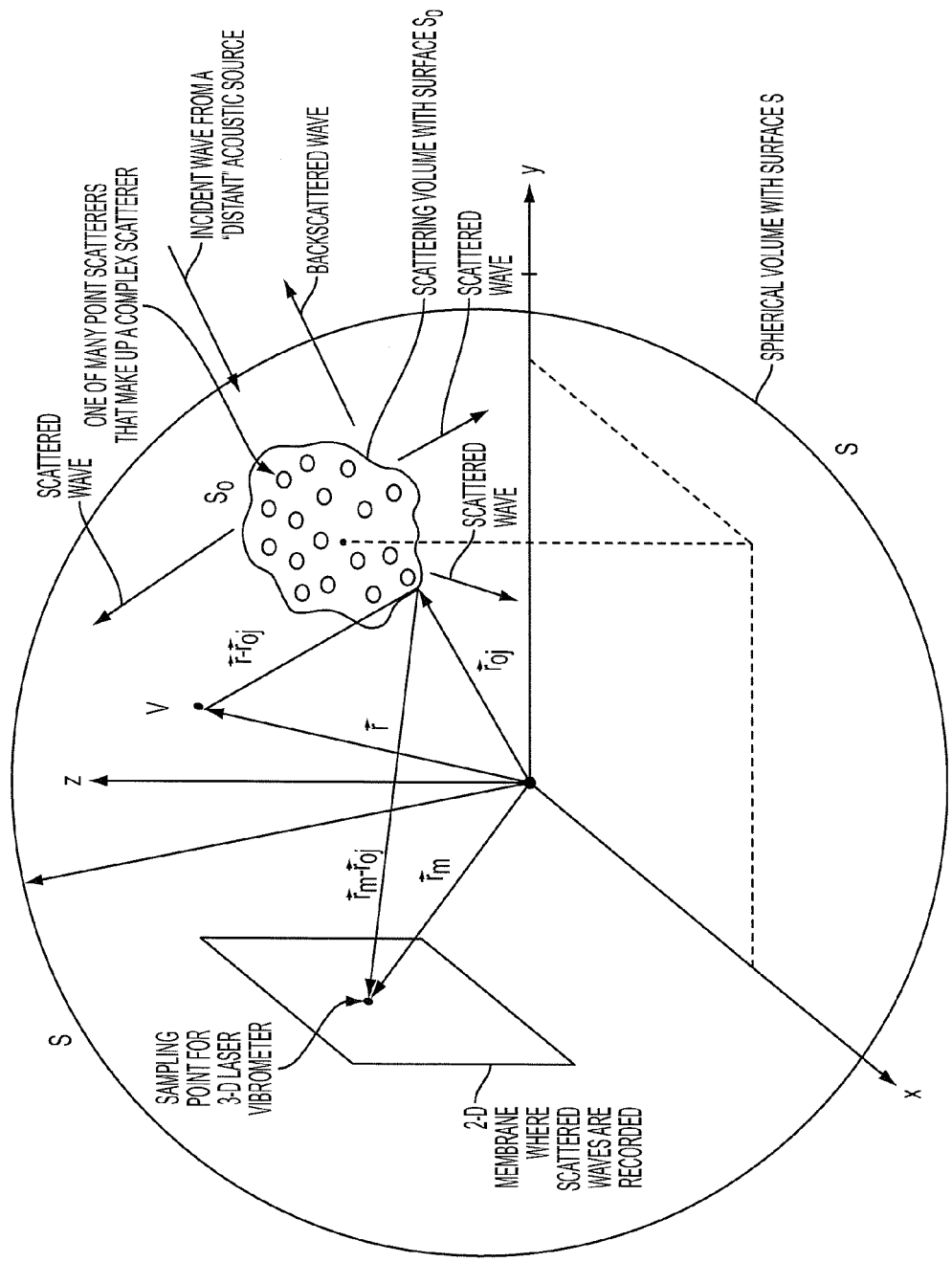
FIG. 18 is a representation of the geometry for transforming a low frequency acoustic scattering into the localization of a complex scattering object.

FIG. 18 shows the geometry for transforming a low-frequency (LF) acoustic scattering experiment into the localization of a complex scattering object. Here, we define a complex scattering object as one that can be approximated by multiple point objects or scatterers (See FIG. 18). We consider a "distant" LF acoustic source to be Gaussian random noise in the 1 Hz to 2,500 Hz temporal frequency band. (Note that the shortest/longest wavelength of this source, in air where the speed of sound is 343 meters/second at 20 degrees Celsius, is 0.14 meters/343 meters, respectively) This source radiates its acoustic energy toward a complex scattering object with an arbitrary volume enclosed by an arbitrary surface $S_0$. As stated above, we assume that the complex scattering object is made up of multiple point scatterers within its volume or on its surface $S_0$.

This complex scattering object scatters the incident LF acoustic waves into a volume V bounded by the surfaces S and $S_0$ (refer to FIG. 18). This scattered acoustic energy propagates outward in multiple directions, eventually impinging on a recording membrane M. A three-dimensional (3-D) laser vibrometer scans the membrane M, estimating $\vec{r}_M$ the scattered acoustic particle velocity $\vec{v}(\vec{r}_M,t)$ (meters/second) at various points on M, where $\vec{r}_M$ is the position vector for a point on M. The localization problem is defined as follows: Given $\vec{v}(\vec{r}_M,t)$ at various points on M, estimate the position vectors $\vec{r}_{Oj}$ (j=1, 2, ..., N), which define the position vectors for the N point scatterers that make up the complex scattering object.

A microphone measures the scalar acoustic pressure $p(\vec{r},t)$ at the spatial point $\vec{r}$ at time t. An acoustic vector sensor measures $p(\vec{r},t)$ as well as the three orthogonal components of a desired acoustic particle motion vector, such as the acoustic particle displacement vector $\vec{s}(\vec{r},t)$, the acoustic particle velocity vector $\vec{v}(\vec{r},t)$, or the acoustic particle acceleration vector $\vec{a}(\vec{r},t)$. An acoustic tensor sensor of order v=2 measures $p(\vec{r},t)$, the three orthogonal components of a desired acoustic particle motion vector, say $\vec{v}(\vec{r},t)$, and the gradient of the acoustic particle motion vector, say $\nabla \vec{v}(\vec{r},t)$, which is an acoustic tensor of order v=2; that is, the 3×3 matrix $$\nabla \vec{v} = \begin{bmatrix} \frac{\partial v_x}{\partial x} & \frac{\partial v_y}{\partial x} & \frac{\partial v_z}{\partial x} \\ \frac{\partial v_x}{\partial y} & \frac{\partial v_y}{\partial y} & \frac{\partial v_z}{\partial y} \\ \frac{\partial v_x}{\partial z} & \frac{\partial v_y}{\partial z} & \frac{\partial v_z}{\partial z} \end{bmatrix}$$

Here, $\vec{v}(\vec{r},t)=v_x\hat{x}+v_y\hat{y}+v_z\hat{z}$ is the acoustic particle velocity vector at some point r in the volume V (bounded by the surfaces S and $S_0$ in FIG. 18), $$\nabla = \frac{\partial}{\partial x}\hat{x} + \frac{\partial}{\partial y}\hat{y} + \frac{\partial}{\partial z}\hat{z}$$

is the gradient operator and $\hat{x}$, $\hat{y}$ and $\hat{z}$ are the orthogonal unit vectors in the x, y and z directions, respectively, of a Cartesian coordinate system. Refer to FIG. 18.

Thus, an acoustic tensor sensor of order v=2 performs the scalar measurement $p(\vec{r},t)$ (which is an acoustic tensor sensor of order v=0), the vector measurement $\vec{v}(\vec{r},t)$ (which is an acoustic tensor sensor of order v=1), and the tensor measurement $\nabla \vec{v}(\vec{r},t)$ (which is an acoustic tensor sensor of order v=2). It follows that an acoustic tensor sensor of order v measures the scalar $p(\vec{r},t)$, the vector $\vec{v}(\vec{r},t)$, the tensor $\nabla \vec{v}(\vec{r},t)$ of order v=2 and all the higher-order acoustic tensors up to order v.

Recall that the aforementioned three-dimensional (3-D) laser vibrometer scans the membrane M, estimating the scattered acoustic particle velocity $\vec{v}(\vec{r}_M,t)$ at various points on M, where $\vec{r}_M$ is the position vector for a point on M. Although the 3-D laser vibrometer does not act as an exact acoustic vector sensor at some point $\vec{r}_M$ on the membrane, since it does not measure the acoustic pressure $p(\vec{r},t)$ at points $\vec{r}_M$ on the membrane, it has sufficient information to compute an unambiguous direction for the acoustic intensity vector. Let us elaborate.

In general, the acoustic intensity vector is given by $\vec{I}(\vec{r},t)=p(\vec{r},t)\vec{v}(\vec{r},t)$ for any point $\vec{r}$ in the volume V (refer to FIG. 18). The magnitude of this vector, namely, $|\vec{I}(\vec{r},t)|$, gives the exact acoustic intensity in watts/square meter. The direction of $\vec{I}(\vec{r},t)$, namely, the unit vector $\hat{n}=\vec{I}(\vec{r},t)/|\vec{I}(\vec{r},t)|$, gives the unambiguous direction of this acoustic intensity. If we do not measure the acoustic pressure $p(\vec{r},t)$, and measure only the acoustic particle velocity vector $\vec{v}(\vec{r},t)$, then the unit vector $\hat{n}_v = \vec{v}(\vec{r},t)/|\vec{v}(\vec{r},t)|$ will be ambiguous. That is, we will not be able to tell the difference between $\hat{u}$ and $-\hat{u}$; we need $p(\vec{r},t)$ to resolve the ambiguity. Fortunately, our acoustic scattering experiment is designed so that we always know that $\hat{n}_v$ will be pointing toward the membrane. Further, to perform localization by our proposed technique, we do not need to know the magnitude of $\vec{v}(\vec{r},t)$. This will be evident in the following sections.

Directional Estimate of a Single LF Acoustic Point Source by estimating $\hat{n}_v$ at one point $\vec{r}_i$ on the membrane. FIG. 18 shows a Velocity Vector Sensor located at the measurement point $\vec{r}_i=(x_i, y_i, z_i)$. Actual point source position is $\vec{r}_s$. FIG. 18 shows a single, stationary velocity vector sensor $V_i$ located at the measurement point $\vec{r}_i=(x_i, y_i, z_i)$. The actual position of the point source, relative to the origin of the inertial coordinate system is $\vec{r}_s$. The actual position of the point source, relative to the vector sensor, is $\vec{R}_{si}=\vec{r}_s-\vec{r}_i$. In the absence of measurement noise or random errors, the velocity vector sensor, implemented with a 3-D laser vibrometer, measures the unit vector $\hat{n}_i=\vec{R}_{si}/|\vec{R}_{si}|$. That is, $\hat{n}_v=\hat{n}_i=\vec{R}_{si}/|\vec{R}_{si}|$ under ideal conditions. Under noisy conditions, the 3-D laser vibrometer could make multiple time domain estimates of $\vec{v}(\vec{r}_i,t)$, average the results, then compute the unit vector $\hat{n}_v$. This would give the best estimate of $\hat{n}_i$. If one is interested in the temporal frequency spectrum of the point source, then one could take the temporal Fourier transform of $\vec{v}(\vec{r}_i,t)$, namely, $$\vec{V}(\vec{r}_i, \omega) \equiv \int_{-\infty}^{\infty} \vec{v}(\vec{r}_i, t) e^{-j\omega t} dt,$$

where ω is the radian temporal frequency with dimensions of radians/second. It is important to note that this temporal frequency domain processing would produce a unit vector for every temporal frequency in the spectrum of $\vec{V}(\vec{r}_i,\omega)$. This will prove very useful for spatially resolving two closely-spaced point scatterers with different temporal frequencies.

In real-world acoustic environments, the velocity vector sensor (e.g., the 3-D laser vibrometer) is exposed to random and systematic errors, measurement noise and interfering directional noise sources (sometimes caused by anisotropic ambient noise fields). If there are no interfering directional noise sources (e.g., multiple, complex acoustic sources in the vicinity of the desired acoustic source) and systematic errors are accounted for, one should compute the time average of $\vec{v}(\vec{r}_i,t)$ or temporal frequency average of $\vec{V}(\vec{r}_i,\omega)$ before calculating $\hat{n}_i$. If the averaging time is "sufficiently long" and the acoustic particle velocity measurement noises are zero mean and uncorrelated, then one should obtain an unbiased estimate of the unit vector $\hat{n}_i$.

If interfering directional noise sources of the same temporal frequency are present, the velocity vector sensor will measure the weighted sum of all the acoustic particle velocity vectors associated with all the directional noise sources (wanted or unwanted) in the medium. This means that the measurement $\vec{v}(\vec{r}_i,t)$ will estimate the acoustic particle velocity vector associated with the centroid or center of gravity of the distributed noise sources. If one estimates $\hat{n}_v$ as explained above, this will produce a bias in the directional estimate of $\hat{n}_i$, where the bias is a function of the relative strength of all the acoustic sources. Thus, if the interfering sources are not cancelled or suppressed, a biased estimate of $\hat{n}_i$ will result.

Estimation of the Position Vector of a Single, LF Acoustic Point Source from an Array (e.g., multiple points on the membrane) of Stationary Velocity Vector Sensors As illustrated in FIG. 18, the true position vector from the origin to a single, LF acoustic point source S is given by $$\vec{r}_s = (x_s, y_s, z_s)$$

or $$r_s = \begin{bmatrix} x_s \\ y_s \\ z_s \end{bmatrix}. \quad (1')$$

The true position vector from the origin to a stationary vector sensor $V_i$ is given by $$\vec{r}_i = (x_i, y_i, z_i)$$

or $$\vec{r}_i = (x_i, y_i, z_i) \text{ or } \underline{r}_i = \begin{bmatrix} x_i \\ y_i \\ z_i \end{bmatrix}. \quad (2')$$

Under ideal conditions (e.g., no noise, no interfering sources), the vector sensor $V_i$ produces the directional estimate $$\hat{n}_i = \vec{R}_{si} / |\vec{R}_{si}|, \quad (3')$$

where $$\vec{R}_{si} = \vec{r}_s - \vec{r}_i = |\vec{R}_{si}| \hat{n}_i \quad (4')$$

is the position vector of the point source S relative to the stationary vector sensor $V_i$ under ideal conditions. In real-world complex acoustic environments, the vector sensor produces the noisy, possibly biased estimate $\hat{u}_i$ instead of the ideal (error-free, unbiased) estimate $\hat{n}_i$. Here, the noisy, possibly biased unit vector $$\hat{u}_i = \hat{\underline{u}}_i = \begin{bmatrix} \hat{u}_{xi} \\ \hat{u}_{yi} \\ \hat{u}_{zi} \end{bmatrix} \quad (5')$$

is represented in 3-tuple, column vector notation.

Under realistic conditions, the position vector of the LF source S relative to the stationary vector sensor V, is $$= \vec{R}_i = R_i \hat{u}_i = R_i \hat{\underline{u}}_i \quad (6')$$

instead of $\vec{R}_{si} = \vec{r}_s - \vec{r}_i = |\vec{R}_{si}|\hat{n}_i$. (Refer to FIG. 19) This implies an error vector $\vec{e}_i$ given by $$\vec{e}_i = \vec{R}_i - \vec{R}_{si} = R_i \hat{u}_i - (\vec{r}_s - \vec{r}_i) \quad (7')$$

in geometric vector notation or $$\underline{e}_i = R_i \hat{\underline{u}}_i - (\underline{r}_s - \underline{r}_i) = (R_i \hat{\underline{u}}_i + \underline{r}_i) - \underline{r}_s \quad (8')$$

in 3-tuple, column vector notation. Note that $R_i$ is a non-negative, real number.

Figure 19:
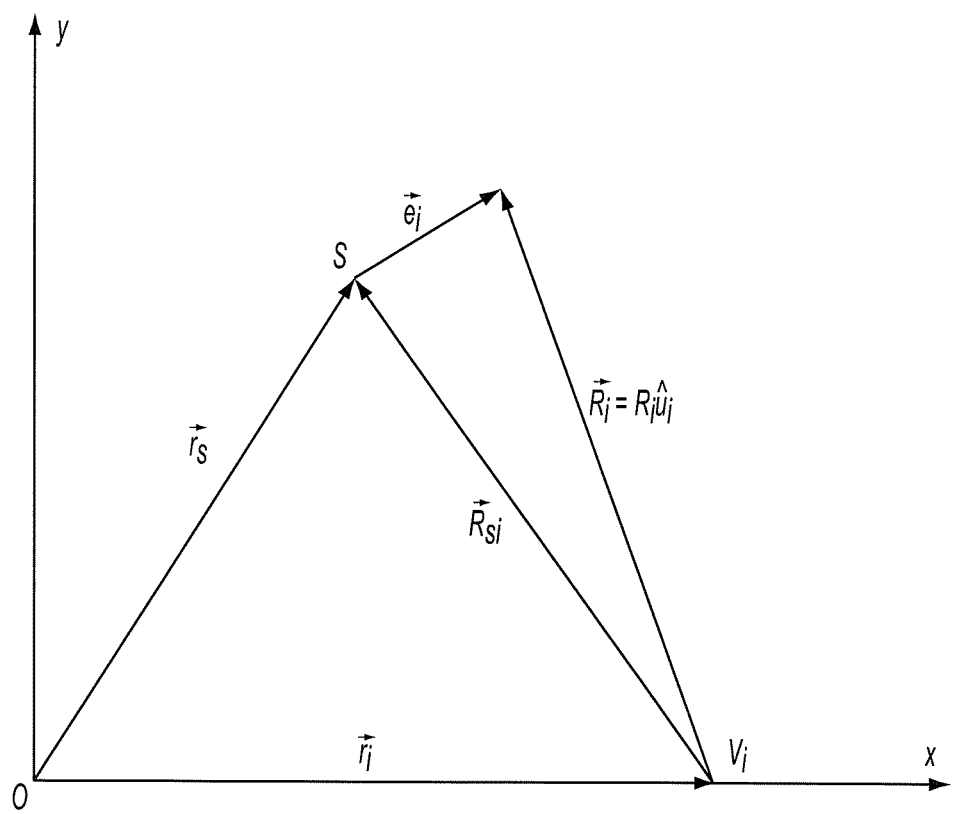
FIG. 19 is a representation of a velocity vector sensor located at a measurement point.

As discussed in previous section on directional estimates, a single vector sensor $V_i$ can estimate the unit vector $\hat{\underline{u}}_i$ with reasonable accuracy (e.g., ±2° for signal-to-noise ratios on the order of 10 dB). Although one can bound the value of the relative range $R_i$ (e.g., $R_{min} \leq R_i \leq R_{max}$), the bounds are generally not accurate enough for localization purposes. [Note: Based on signal-to-noise ratio (SNR) and acoustic propagation models, we can estimate the bounds $R_{min}$ and $R_{max}$. However, fluctuations in SNR and model inaccuracies would produce large variations (much greater than the 10% error desired for localization) in $R_i$, especially in complex acoustic environments.] Thus, we will assume that the relative, nonnegative range $R_i$ is essentially unknown. This implies that the error (equations 3'-8') has two unknowns, namely, the scalar $R_i$ and the vector $\underline{r}_s$. However, if we constrain $R_i$ such that the error vector $\vec{e}_i$ is orthogonal to the relative position vector $\vec{R}_i$, that is, $$\vec{e}_i \cdot \vec{R}_i = 0, \quad (9')$$

then for a given value of $\underline{r}_s$ and a given value of $\hat{\underline{u}}_i$, the quantity $|\vec{e}_i|^2 = \underline{e}_i^T \underline{e}_i$ will always be a minimum (Refer to FIG. 19). Here, $\underline{e}_i^T$ is the transpose of the column vector $\underline{e}_i$. Using (6'), (7') and (8'), we can rewrite (9') in 3-tuple, column vector notation. Doing so, we get $$R_i \hat{\underline{u}}_i^T [(R_i \hat{\underline{u}}_i + \underline{r}_i) - \underline{r}_s] = 0 \quad (10')$$

Solving (10') for $R_i$ gives the scalar $$R_i = \hat{\underline{u}}_i^T (\underline{r}_s - \underline{r}_i). \quad (11')$$

Using the constraint (11'), we can rewrite the error vector (8') as $$e_i = \hat{u}_i^T(r_s - r_i)\hat{u}_i + r_i - r_s = (I - \hat{u}_i\hat{u}_i^T)(r_i - r_s), \quad (12')$$

where I is the 3×3 identity matrix.

With the constraint (11'), the error vector $e_i$ in (12') has only one unknown, namely, $r_s$ or the true position vector from the origin to a single, acoustic point source S. If there are m stationary velocity vector sensors (or we consider measuring the acoustic particle velocity vectors at in spatial points on the membrane), then we can use the theory of weighted least-squares to estimate $r_s$. That is, the value $\hat{r}_s$ that minimizes the quantity $E(r_s)$, namely, $$E(r_s) = \sum_{i=1}^{m} w_i E_i = \sum_{i=1}^{m} w_i e_i^T e_i = \sum_{i=1}^{m} w_i (r_i - r_s)^T (I - \hat{u}_i u_i^T)^T (I - \hat{u}_i u_i^T)(r_i - r_s), \quad (13')$$

is the weighted least-squares estimate of $r_s$. Here, we assume that the weights $w_i$ are nonnegative real numbers that satisfy the condition $$\sum_{i=1}^{m} w_i = 1. \quad (14')$$

Since $(I - \hat{u}_i u_i^T)$ is a symmetric 3×3 matrix, then $(I - \hat{u}_i u_i^T)^T = (I - \hat{u}_i u_i^T)$. Since $\hat{u}_i$ is a unit vector, then $(I - \hat{u}_i u_i^T)^2 = (I - \hat{u}_i u_i^T)$. Using these matrix properties in (13'), we get $$E(r_s) = E(x_s, y_s, z_s) = \sum_{i=1}^{m} w_i E_i = \sum_{i=1}^{m} w_i e_i^T e_i = \sum_{i=1}^{m} w_i (r_i - r_s)^T (I - \hat{u}_i u_i^T)(r_i - r_s). \quad (15')$$

The weighted least-squares estimate $\hat{r}_s$ of the source position vector $r_s$ is found by solving the equation $$DE(r_s) = DE(x_s, y_s, z_s) = \sum_{i=1}^{m} w_i DE_i = \sum_{i=1}^{m} w_i D(e_i^T e_i) = 0 \quad (16')$$

where $$D = \begin{bmatrix} \frac{\partial}{\partial x_s} \\ \frac{\partial}{\partial y_s} \\ \frac{\partial}{\partial z_s} \end{bmatrix} \quad (17')$$

and 0 is the 3×1 null vector.

A useful result in the theory of quadratic forms is that if $Q = r_s^T M r_s$ and M is a symmetric matrix, then $DQ = 2Mr_s$. Applying this result to (15') and (16') gives $$DE = \sum_{i=1}^{m} w_i DE_i = \sum_{i=1}^{m} w_i 2(I - \hat{u}_i u_i^T)(r_i - \hat{r}_s) = 0 \quad (18')$$

Equation (18') can be rewritten as $$\left[\sum_{i=1}^{m} w_i (I - \hat{u}_i u_i^T)\right] \hat{r}_s = \sum_{i=1}^{m} w_i (I - \hat{u}_i u_i^T) r_i. \quad (19')$$

If we define the 3×3 matrix $$A \equiv \left[\sum_{i=1}^{m} w_i (I - \hat{u}_i u_i^T)\right] \quad (20')$$

and the 3×1 column vector $$\underline{b} \equiv \left[\sum_{i=1}^{m} w_i (I - \hat{u}_i u_i^T) r_i\right], \quad (21')$$

then (19') can be expressed as the simplified matrix equation $$A\hat{r}_s = \underline{b} \quad (22')$$

Finally, the weighted least-squares estimate $\hat{r}_s$ of the source position vector $r_s$ is found by solving the simplified matrix equation (22'). Doing so, we get $$\hat{r}_s = A^{-1} \underline{b}. \quad (23')$$

Let us now summarize our result. First, let us assume no noise or interfering sources and exact knowledge of the vector sensor position vectors $r_i$ or $\vec{r}_i$. Under these conditions, at least two velocity vector sensors (m=2), separated by some nonzero distance $|\vec{r}_2 - \vec{r}_1|$, are required to estimate the source position vector $r_s$. Specifically, each vector sensor only needs one time sample to estimate its corresponding unit vectors $\hat{u}_1(t_j)$ and $\hat{u}_2(t_j)$, where $t = t_j$ is the sampling time. For these ideal conditions, additional vector sensors (m>2) and additional time samples would not contribute any additional information.

Second, let us consider the more realistic case of anisotropic noise fields and/or interfering noise sources as well as inexact knowledge of the vector sensor position vectors $r_i$ or $\vec{r}_i$. For this case, we still need at least two vector sensors (m=2), separated by some nonzero distance $|\vec{r}_2 - \vec{r}_2|$, to estimate the source position vector $r_s$. Under these conditions, we can approach the estimate of $r_s$ in several ways.

For each sensor, we could gather n noisy time samples of the unit vector $\hat{u}_i(t)$, that is, $\hat{u}_i(t_1), \hat{u}_i(t_2), \ldots, \hat{u}_i(t_j), \ldots, \hat{u}_i(t_n)$ and compute the time-averaged unit vector $\hat{u}_{iave}$, where $$\hat{u}_{iave} = \frac{1}{n} \sum_{j=1}^{n} \hat{u}_i(t_j) \quad (i = 1, 2, \ldots, m). \quad (24')$$

We could then generate an estimate for $\hat{r}_s$ by replacing a $\hat{u}_i$ with $\hat{u}_{iave}$ in equations (20') and (21') and inverting (22') to obtain (23').

Alternatively, we could reformulate our weighted least-squares estimate of $\underline{r}_s$ by considering the time-summed error function $E^t(\underline{r}_s)$, namely, $$E^t(\underline{r}_s) = E^t(x_s, y_s, z_s) = \sum_{j=1}^{n}\sum_{i=1}^{m} w_i E_i = \qquad(25')$$

$$\sum_{j=1}^{n}\sum_{i=1}^{m} w_i \underline{e}_i^T \underline{e}_i = \sum_{i=1}^{m} w_i (\underline{r}_i - \underline{r}_s)^T \left[\sum_{j=1}^{n}\left(I - \hat{\underline{u}}_i \hat{\underline{u}}_i^T\right)\right](\underline{r}_i - \underline{r}_s)$$

where we have summed the squared error over m vector sensors and n time samples for each sensor. Following the same least-squares solution as above, $\hat{\underline{r}}_s$ can be found by solving the matrix equation $$A_t \hat{\underline{r}}_s = \underline{b}_t, \qquad(26')$$

where $$A_t \equiv \left[\sum_{i=1}^{m} w_i \left(I - \frac{1}{n}\sum_{j=1}^{n} \hat{u}_i(t_j)\hat{u}_i^T(t_j)\right)\right] \qquad(27')$$

and $$\underline{b}_t \equiv \left[\sum_{i=1}^{m} w_i \left(I - \frac{1}{n}\sum_{j=1}^{n} \hat{u}_i(t_j)\hat{u}_i^T(t_j)\right)\underline{r}_i\right] \qquad(28')$$

Ultimately, what really determines one approach over the other is the vector-sensor operating environment and the fluctuations in signal-to-noise ratio (SNR) that occur in that environment.

Figure 20:
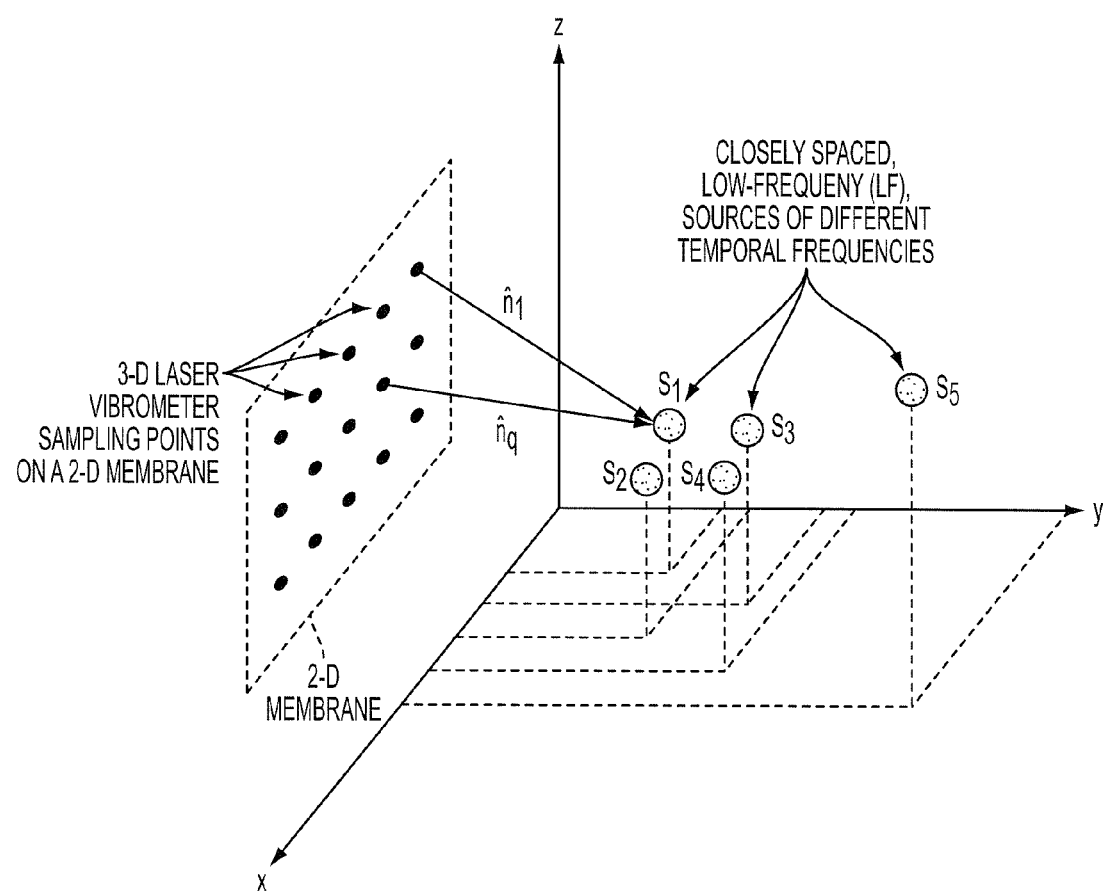
FIG. 20 is a representation of temporal frequency domain processing.

As noted in the previous sections, the temporal Fourier transform of $\vec{v}(\vec{r},t)$, namely, $\vec{V}(\vec{r}_i,\omega)$, at every measurement point $\vec{r}_i$ on the 2-D membrane M will produce multiple unit vectors that are a function of the temporal radian frequency $\omega$. If there are many closely-spaced point scatterers that scatter the LF acoustic energy with different temporal frequencies, then it is possible to spatially resolve these scatterers by exploiting these temporal frequency differences. This spatial resolution at the stated LF scattered acoustic energy implies that imaging is possible when the ensonifying wavelength is much larger than the characteristic length of the object. This imaging capability can only be achieved when velocity vector sensing (or acoustic particle motion sensing) is used vice conventional scalar acoustic pressure sensing that does not measure the vector (directional) part of the wavefield. FIG. 20 shows a geometry with multiple closely-spaced scatterers. If there are no differences in temporal frequency, then the above localization processing will produce the centroid or center of gravity of the complex scattering object.

Figure 21:
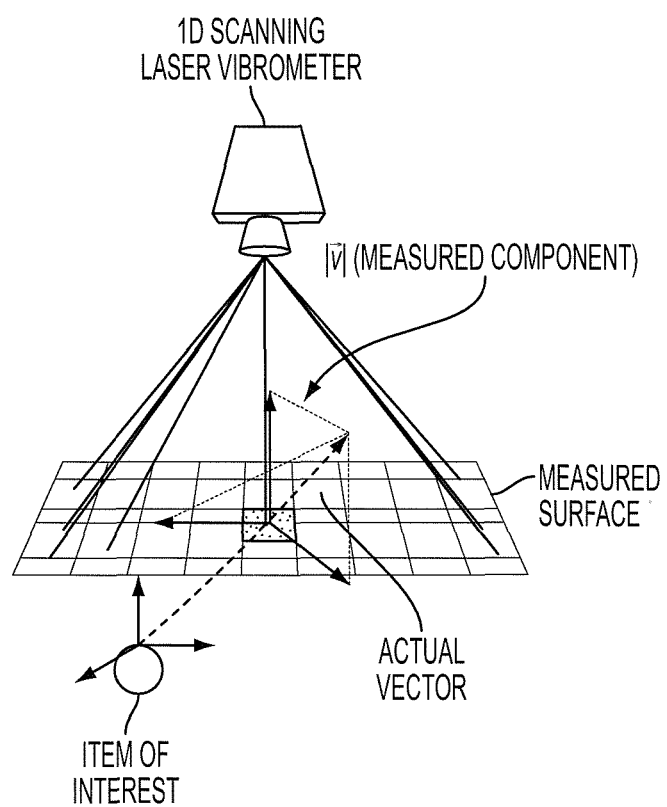
FIG. 21 is a schematic representation of localization using higher-order tensors.

In the exemplary embodiment of FIG. 21, localization is performed using higher-order tensors and measuring the z component of the velocity vector. In the illustrated embodiment, only the orthogonal component of the velocity vector is measured with a single point scanning laser Doppler vibrometer. The object is close to the measured surface (~2 cm), and the location is known, so the direction provided by a 3D vector is not necessary.

Figure 22:
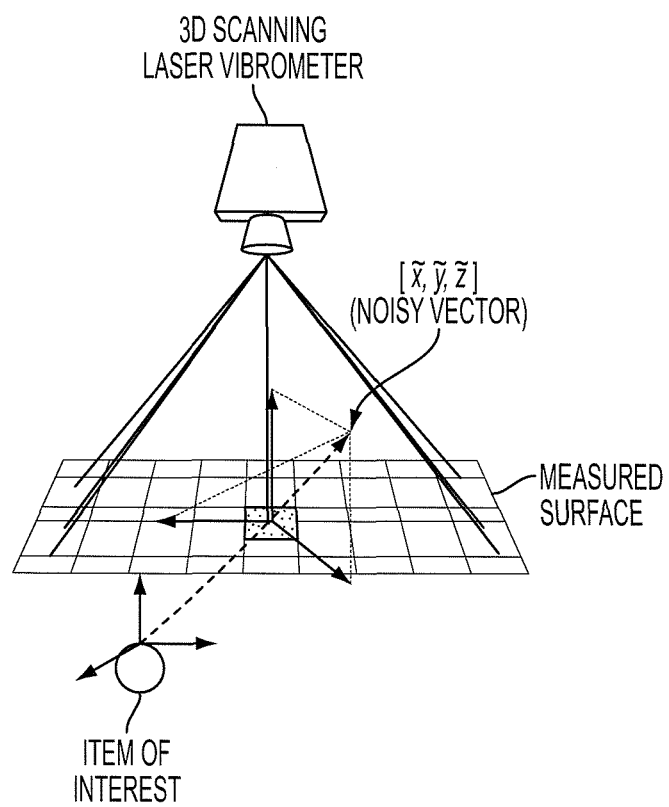
FIG. 22 is a further schematic representation of localization using higher-order tensors.

In the exemplary embodiment of FIG. 22, localization is performed using higher-order tensors and measuring the x, y, and z components of a velocity vector at the volume surface. In the illustrated embodiment, 3D laser Doppler vibrometry estimates the x, y, and z vector components at the measured surface, but cannot be used to measure higher-order tensors, as it cannot measure the gradient components in the z direction. Note that estimating velocity vector components from x,y,z surface displacement introduces errors due to non-linear geometric, material elastic properties, surface modal response from the surface material, and the 2D nature of the surface. That is, measurement accuracy will vary non-linearly depending upon where on the surface they are taken, when in the surface model cycle they are taken, what the surface is made out of and the modal behavior of the surface, some or all of which, may be unknown a-priori.

Figure 23:
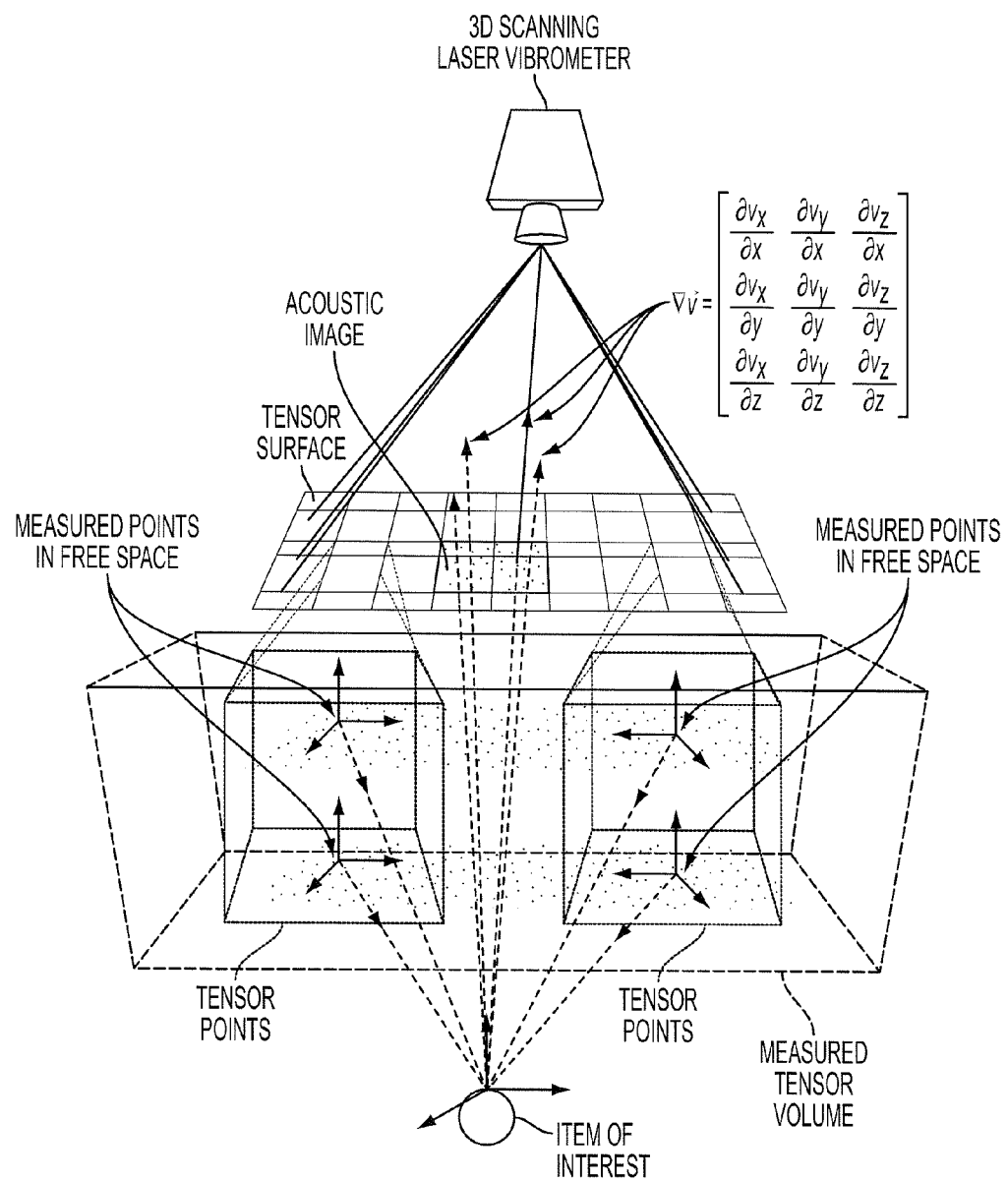
FIG. 23 is a further schematic representation of localization using higher-order tensors.

In the exemplary embodiment of FIG. 23, localization is performed using higher-order tensors and measuring the x, y, and z components of a velocity vector in free space. A 3D laser Tensor vibrometer directly measures the x, y and z vector components at points in free space, and enables measurements to estimate the higher-order tensor components. These higher-order tensor data allow circumvention of the Fourier and Nyquist constraints, allowing resolution of the point-scatterers at low-frequencies which make low frequency imaging possible.

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:
1. A system, comprising:
at least one acoustic source for directing acoustic energy to penetrate at least one surface of a container and at least partially fill the container with acoustic energy to penetrate at least one surface of a container and at least partially fill the container with acoustic energy during an inspection of the container by the system, wherein a frequency of the acoustic energy directed by the at least one acoustic source is selected to achieve a desired level of ensonification of the container, and the frequency of the acoustic energy is selected, at least in part, on type of the container, and the at least one acoustic source is positioned with respect to the container to achieve the desired level of ensonification of the container;
a first sensor to detect acoustic energy from the at least one acoustic source affected by at least one object in the container during the inspection of the container, wherein the first sensor is external to the container and includes one or more velocity vector sensors configured to measure temporal frequency differences of point scatterers that scatter the acoustic energy and spatially resolve the point scatterers at least in part from the measured temporal frequency differences, wherein at least one of the velocity vector sensors is provided as a laser vibrometer which detects a surface vibration on a recording surface on an exterior surface of the container;
a second sensor to confirm presence of the at least one object during the inspection of the container; and a processing module to process at least the detected acoustic energy from the first sensor to identify and to detect a location of the at least one object in the container, wherein the location of the at least one object in the container is determined by interpolating select data from the detected acoustic energy, wherein the select data is interpolated to find energy peaks which are indicative of the location of the at least one object, wherein the at least one object includes a first object and a second, different object, and the first sensor is configured to detect acoustic energy from the acoustic source affected by the first object in the container and the second object in the container without contacting the container, and wherein the processing module is configured to process the detected acoustic energy, the detected surface vibrations and the spatially resolved point scatterers from the first sensor to identify the first object based, at least in part, on an acoustic profile characteristic of the first object, and to identify the second object, at least in part, on an acoustic profile characteristic of the second object.

2. The system according to claim 1, wherein the second sensor comprises a heartbeat sensor.

3. The system according to claim 1, wherein the second sensor comprises a chemical sensor.

4. The system according to claim 1, wherein the second sensor comprises a system to determine weight.

5. The system according to claim 1, wherein the second sensor comprises an infrared sensor.

6. The system according to claim 1, wherein the second sensor comprises a sensor to detect breathing.

7. The system according to claim 1, wherein the second sensor comprises at least one video system.

8. The system according to claim 7, wherein the processing module compares a number of the objects detected by acoustic energy and a number of objects identified in images from the at least one video system.

9. The system according to claim 8, wherein the objects comprise human passengers and the container comprises a vehicle.

10. The system according to claim 9, further including an alert module to generate an alert if the number of passengers detected by the first and second sensors does not match.

11. The system according to claim 1, wherein the second sensor comprises a magnetic sensor.

12. The system according to claim 1, wherein the second sensor comprises an illuminator and a sensor to detect electromagnetic signal characteristics from the container and the object.

13. The system of claim 1, wherein the container is completely enclosed during the inspection of the container, and the detected acoustic energy is processed at predetermined time intervals.

14. The system of claim 1 wherein the container is a vehicle and the acoustic energy is directed towards the vehicle while the vehicle is in motion.

15. The system of claim 14 wherein the at least one acoustic source includes an acoustic transducer and road noise, and the frequency of the acoustic energy directed by the acoustic transducer is selected to achieve the desired level of ensonification of the container.

16. A method, comprising:
directing acoustic energy using at least one acoustic source to penetrate at least one surface of a container and at least partially fill the container with acoustic energy during an inspection of the container, wherein a frequency of the acoustic energy directed at the container is selected to achieve a desired level of ensonification of the container, and the frequency of the acoustic energy is selected, at least in part, on type of the container, and the at least one acoustic source is positioned with respect to the container to achieve the desired level of ensonification of the container;

detecting, by a first sensor, acoustic energy from the at least one acoustic source affected by at least one object in the container during the inspection of the container, wherein the first sensor is external to the container and includes one or more velocity vector sensors configured to measure temporal frequency differences of point scatterers that scatter the acoustic energy and spatially resolve the point scatterers at least in part from the measured temporal frequency differences, wherein the at least one of the velocity vector sensors is provided as a laser vibrometer which detects a surface vibration on a recording surface on an exterior surface of the container;

using a second sensor to confirm presence of the at least one object in the container during the inspection of the container; and processing at least the detected acoustic energy from the first sensor to identify and to detect a location of the at least one object in the container, wherein the location of the at least one object in the container is determined by interpolating select data from the detected acoustic energy, wherein the select data is interpolated to find energy peaks which are indicative of the location of the at least one object, wherein the at least one object includes a first object and a second, different object, and the first sensor is configured to detect acoustic energy from the acoustic source affected by the first object in the container and the second object in the container without contacting the container, and wherein the detected acoustic energy, the detected surface vibrations and the spatially resolved point scatterers received from the first sensor are processed to identify the first object based, at least in part, in an acoustic profile characteristic of the first object, and to identify the second object, at least in part, on an acoustic profile characteristic of the second object.

17. The method according to claim 16, wherein the second sensor comprises one or more of a heartbeat sensor, a chemical sensor, a system to determine weight, an infrared sensor, a breathing detector, and/or at least one video system.

18. The method according to claim 16, wherein the second sensor comprises a heartbeat sensor and the object comprises at least one person, wherein the processing step further includes comparing a number of persons detected by acoustic energy to a number of heartbeats detected.

19. The method according to claim 16, wherein the second sensor comprises at least one video system, wherein the processing step further includes comparing a number of persons detected by acoustic energy to a number of persons identified in video images from the video system.

20. A system, comprising:
a means for directing acoustic energy to penetrate at least one surface of a container and at least partially fill the container with acoustic energy during an inspection of the container by the system, wherein a frequency of the acoustic energy directed by the means for directing acoustic energy is selected to achieve a desired level of ensonification of the container, and the frequency of the acoustic energy is selected, at least in part, on type of the container, and the means for directing acoustic energy is positioned with respect to the container to achieve the desired level of ensonification of the container;

a first sensor means for detecting acoustic energy affected by at least one object in the container during the inspection of the container, wherein the first sensor means is external to the container and includes one or more velocity vector sensors configured to measure temporal frequency differences of point scatterers that scatter the acoustic energy and spatially resolve the point scatterers at least in part from the measured temporal frequency differences, wherein at least one of the velocity vector sensors is provided as a laser vibrometer which detects a surface vibration on a recording surface of an exterior surface of the container;

a second sensor means for confirming presence of the at least one object in the container during the second inspection of the container; and a processing means for processing at least the detected acoustic energy from the first sensor means to identify and to detect a location of the at least one object in the container, wherein the location of the at least one object in the container is determined by interpolating select data from the detected acoustic energy, wherein the select data is interpolated to find energy peaks which are indicative of the location of the at least one object, wherein the at least one object includes a first object and a second, different object, and the first sensor means is configured to detect acoustic energy from the acoustic source affected by the first object in the container and the second object in the container without contacting the container, and wherein the processing means is configured to process the detected acoustic energy, the detected surface vibrations and the spatially resolved point scatterers from the first sensor means to identify the first object based, at least in part, on an acoustic profile characteristic of the first object, and to identify the second object, at least in part, on an acoustic profile characteristic of the second object.

* * * * *